(12) United States Patent
Micoli et al.

(10) Patent No.: US 9,475,846 B2
(45) Date of Patent: Oct. 25, 2016

(54) CONJUGATED VI SACCHARIDES

(71) Applicant: NOVARTIS AG, Basel (CH)

(72) Inventors: Francesca Micoli, Siena (IT);
Francesco Berti, Colle Val d'Elsa (IT);
Paolo Costantino, Colle Val d'Elsa (IT)

(73) Assignee: GlaxoSmithKline Biologicals SA, Rixensart (BE)

( * ) Notice: Subject to any disclaimer, the term of this patent is extended or adjusted under 35 U.S.C. 154(b) by 221 days.

(21) Appl. No.: 13/661,409

(22) Filed: Oct. 26, 2012

(65) Prior Publication Data

US 2013/0142822 A1    Jun. 6, 2013

Related U.S. Application Data

(63) Continuation of application No. 12/997,411, filed as application No. PCT/IB2009/006285 on Jun. 12, 2009, now abandoned.

(30) Foreign Application Priority Data

Jun. 13, 2008   (GB) .................................. 0810894.6

(51) Int. Cl.
*A61K 47/48*   (2006.01)
*A61K 39/112*  (2006.01)
*C07K 14/195*  (2006.01)

(52) U.S. Cl.
CPC ......... *C07K 14/195* (2013.01); *A61K 39/0275* (2013.01); *A61K 47/4833* (2013.01); *A61K 47/48261* (2013.01)

(58) Field of Classification Search
CPC ..................... A61K 2039/70; A61K 39/0275; A61K 39/092; A61K 39/095; A61K 39/102; A61K 47/4823; A61K 47/48238; A61K 47/4833; C07K 14/3156
See application file for complete search history.

(56) References Cited

U.S. PATENT DOCUMENTS

| 8,945,582 B2 | 2/2015 | De Hemptinne et al. | |
| 2006/0165730 A1* | 7/2006 | Porro | A61K 39/092 424/249.1 |
| 2007/0141084 A1* | 6/2007 | Lee et al. | 424/236.1 |
| 2009/0311285 A1* | 12/2009 | Biemans et al. | 424/194.1 |

FOREIGN PATENT DOCUMENTS

| WO | 94/03208 A1 | 2/1994 |
| WO | 96/11709 A1 | 4/1996 |
| WO | 02/20059 A2 | 3/2002 |

OTHER PUBLICATIONS

Lillo et al. Carbohydr. Polymers 51: 317-325, 2003.*
Canh et al., "Effect of Dosage in Immunogenicity of a Vi Conjugate Vaccine Injected Twice intoo 2- to 5-Year Old Vietnamese Children," Infection and Immunity 72(11):6586-6588 (2004).
Guzman et al., "Vaccines Against Typhoid Fever," Vaccine 24(18):3804-3811 (2006).
Kageyama et al., "Diphtheria Toxin Mutant CRM197 Possesses Weak EF2-ADP-ribosyl Activity that Potentiates its Antitumorigenic Activity," J. Biochem. 142:95-104 (2007).
Kao et al., Quantification of O-acetyl, N-acetyl and Phosphate Groups and Determination of the Extend of O-acetylation in Bacterial Vaccine Polysaccharides by High-Performance Anion-Exchange Chromatography with Conductivity Detection (HPAEC-CD), Vaccine 22:335-344 (2004).
Lillo et al., "Chemical Modifications of 1->4-2-amino-2-deoxy-alpha-d-galactan," Carbohydrate Polymers, Applied Science Publishers, Ltd., Barking, GB, 51(3):317-325 (2003).
Szu et al., "Relation Between Structure and Immunologic Properties of the Vi Capsular Polysaccharide," Infect. Immun. 59(12):4555-4561 (1991).
Szu et al., "Synthesis and Some Immunologic Properties of an O-Acetyl Pectin [Poly(1-4)-a-D-GalpA]-Protein Conjugate as a Vaccine for Typhoid Fever," Infect. Immun. 62(12):5545-5549 (1994).
International Preliminary Report on Patentability, issued Dec. 14, 2010, for International Application No. PCT/IB2009/006285, filed Jun. 12, 2009.
International Search Report, mailed Mar. 24, 2010, for International Application No. PCT/IB2009/006285, filed Jun. 12, 2009.
Written Opinion of the International Searching Authority, mailed Dec. 13, 2010, for International Application No. PCT/IB2009/006285, filed Jun. 12, 2009.

* cited by examiner

*Primary Examiner* — S. Devi
(74) *Attorney, Agent, or Firm* — Morrison & Foerster LLP

(57) ABSTRACT

Two Vi conjugates have been prepared by carbodiimide-mediated synthesis, using adipic acid dihydrazide derivatized $CRM_{197}$ (a non-toxic variant of diphtheria toxin) and tetanus toxoid, as carrier proteins.

5 Claims, 11 Drawing Sheets

CONJUGATED VI SACCHARIDES

This application is a Continuation application of U.S. application Ser. No. 12/997,411, filed on Jun. 12, 2009, now abandoned, which is a 371 of International Application No. PCT/IB2009/006285, filed on Jun. 12, 2009, which claims the benefit of United Kingdom patent application 0810894.6, filed 13 Jun. 2008, the complete contents of which are incorporated herein by reference.

TECHNICAL FIELD

The invention relates to vaccines, more particularly those against typhoid fever.

BACKGROUND ART

Typhoid fever is a common serious disease in many parts of the world. Purified capsular polysaccharide from *Salmonella typhi* (Vi) is used as a vaccine, providing about 70% protection against typhoid fever in individuals 5- to 45-years-old. However, the vaccine is unable to establish immunological memory and is ineffective in infants or toddlers [1]. A conjugate vaccine of Vi coupled to recombinant mutant *Pseudomonas aeruginosa* exoprotein A (Vi-rEPA) gave a booster response in young children and was highly efficacious [2].

It is an object of the invention to provide new processes for the production of Vi conjugate vaccines that may be employed on an industrial scale.

DISCLOSURE OF THE INVENTION

The inventors have devised a new method for manufacturing Vi-conjugates and have also produced a new conjugate comprising Vi coupled to $CRM_{197}$.

A first aspect of the invention provides a method for the preparation of a Vi conjugate. A linker, such as adipic acid dihydrazide (ADH), and a carbodiimide, such as 1-ethyl-3 (3-dimethylaminopropyl)carbodiimide (EDAC), are simultaneously added to a solution containing a carrier protein, such as $CRM_{197}$ or tetanus toxoid (TT), to give a derivatised carrier protein.

A buffer, such as 2-(N-morpholino)ethanesulfonic acid (MES), may be added to the solution containing the carrier protein prior to the addition of ADH and EDAC. The weight ratio of the carbodiimide to the protein is typically 0.1 to 0.15, as higher carbodiimide/protein ratios can cause aggregate formation.

Following the derivatisation of the carrier protein, any excess linker (e.g. ADH) is removed by, for example, dialysis or tangential flow filtration (TFF).

Vi is also activated with a carbodiimide and is subsequently combined with the derivatised carrier protein. For Vi activation, various ratios of Vi and carbodiimide can be used. A 1:1 molar ratio (COOH groups of Vi to carbodiimide) can be used, but to reduce the amount of residual unconjugated carbodiimide derivatives (e.g. ureas such as EDU; N-ethyl-N'-(3-dimethylaminopropyl)urea, a soluble reaction product of EDAC coupling) higher ratios can be used i.e. with a molar excess of Vi e.g. >1.5:1 and ideally ≥3:1, such as 3:1, 4:1, 5:1, 6:1, 7:1, 8:1, 9:1 or higher. Ratios up to 200:1 might be used. These ratios are higher than the ones used in reference 3. Vi activation can be performed at room temperature e.g. in about 2 minutes.

Thus, the method comprises the steps of:
a) Simultaneously combining a linker, a carbodiimide and a carrier protein.
b) Reacting Vi with a carbodiimide
c) Reacting the product of step a) with the product of step b).

Steps a) and b) may be performed in any order.

After step a), but before step c), any excess linker may be removed.

This aspect of the invention also provides a method for preparing a Vi–$CRM_{197}$ conjugate, wherein Vi is combined with derivatised $CRM_{197}$. The method comprises the steps of:
a) Reacting Vi with a carbodiimide
b) Reacting the product of step a) with derivatised $CRM_{197}$.

This aspect of the invention also provides a method for preparing a Vi–$CRM_{197}$ conjugate, comprising the step of:
a) Reacting activated Vi with derivatised $CRM_{197}$.

Reference 3 describes a process for preparing conjugates of Vi with rEPA and bovine serum albumin (BSA) by carbodiimide-mediated synthesis with ADH as the linker. However, this process does not involve the simultaneous combination of rEPA/BSA, ADH and EDAC. Rather, rEPA/BSA and ADH are combined and mixed prior to the addition of EDAC.

A second aspect of the invention provides a Vi–$CRM_{197}$ conjugate. This conjugate may be prepared by the above method, or may be obtained by other means.

Vi Saccharide

Vi is the capsular saccharide of *Salmonella typhi* (previously classified as a species itself, but now referred to as the *typhi* serovar of *S. enterica*). Vi may also be found in other serovars of *Salmonella* (such as *S. enterica* serovar *paratyphi* C or serovar *dublin*) and in other bacteria, such as *Citrobacter* (e.g. *C. freundii* and *C. youngae*). The Vi polysaccharide is a linear homopolymer of a hexosaminuronic acid, α1,4-N-acetylgalactos-aminouronic acid, which is 60-90% acetylated at the C-3 position [4-9]. The O-acetyl substitution on Vi is a factor in its ability to elicit a protective immune response [10]. The immunogenicity of Vi is closely related to its degree of O-acetylation. Partial de-O-acetylation can slightly increase immunogenicity; complete de-O-acetylation eliminates the immunogenicity of Vi [11].

The Vi saccharide used in the present invention may be chemically modified relative to the capsular saccharide as found in nature. For example, the Vi saccharide may be partially de-O-acetylated, de-N-acetylated (partially or fully), N-propionated (partially or fully), etc. De-acetylation may occur before, during or after conjugation, but preferably occurs before conjugation. The effect of de-acetylation etc. can be assessed by routine assays.

The Vi saccharide may be hydrolysed to form shortened polysaccharides (e.g. with a degree of polymerisation (DP) of at least 10, e.g. 20, 30, 40, 50, 60 or more) or oligosaccharides (e.g. with a degree of polymerisation of from 2 to 10). Oligosaccharides are preferred to polysaccharides for use in vaccines. The average degree of polymerisation can conveniently be measured by ion exchange chromatography or by colorimetric assays [12].

In addition, it has been found by double immunodiffusion that pectin, when O-acetylated at C-2 and C-3, is antigenically identical to Vi. The structure of Vi differs from that of pectin in that it is N-acetylated at C-2 and O-acetylated at C-3. O-acetylated pectin conjugated to tetanus toxoid elicited Vi antibodies in mice, and reinjection elicited a booster response [13,14]. Accordingly, O-acetylated pectin may be used in the invention in place of Vi. However, Vi conjugates have been shown to be significantly more immunogenic than their O-acetylated pectin analogs, and so Vi from natural sources is preferred [13]. Nevertheless, it will be understood that references to "Vi" may include "O-acetylated pectin" and any other molecules that may be structurally or antigenically identical to Vi and are capable of eliciting antibodies that recognise native Vi.

"Vi" may refer to a Vi polysaccharide (e.g. with a degree of polymerisation of at least 10, e.g. 20, 30, 40, 50, 60 or more) or a Vi oligosaccharide (e.g. with a degree of polymerisation of from 2 to 10) and may have been chemically modified. Oligosaccharides may be the result of depolymerisation and/or hydrolysis of a parent polysaccharide.

Vi Purification

Capsular saccharides can be purified by known techniques, as described in the references herein. A typical process involves base extraction, centrifugation, filtration, RNase/DNase treatment, protease treatment, concentration, size exclusion chromatography, ultrafiltration, anion exchange chromatography, and further ultrafiltration.

A particularly useful method is disclosed in reference 15, which is incorporated herein by reference.

A process for purifying Vi may comprise the steps of (a) precipitation of Vi, followed by (b) solubilisation of the precipitated Vi using an alcohol, such as ethanol.

Precipitation and Alcohol Solubilisation

Many techniques for precipitating soluble polysaccharides, such as Vi, are known in the art. Preferred methods use one or more cationic detergents. The detergents preferably have the following general formula:

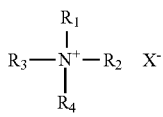

wherein: $R_1$, $R_2$ and $R_3$ are the same or different and each signifies alkyl or aryl; or $R_1$ and $R_2$ together with the nitrogen atom to which these are attached form a 5- or 6-membered saturated heterocyclic ring, and $R_3$ signifies alkyl or aryl; or $R_1$, $R_2$ and $R_3$ together with the nitrogen atom to which these are attached form a 5- or 6-membered heterocyclic ring, unsaturated at the nitrogen atom, $R_4$ signifies alkyl or aryl, and $X^-$ signifies an anion.

Particularly preferred detergents for use in the method are tetrabutylammonium and cetyltrimethylammonium salts (e.g. the bromide salts). Cetyltrimethylammonium bromide ('CTAB') is particularly preferred [16]. CTAB is also known as hexadecyltrimethylammonium bromide, cetrimonium bromide, Cetavlon and Centimide. Other detergents include hexadimethrine bromide and myristyltrimethylammonium salts.

Vi can be released into media during culture. Accordingly, the starting material for precipitation will typically be the supernatant from a centrifuged bacterial culture or will be a concentrated culture. This material may be filtered to remove turbidity.

The precipitation step may be selective for Vi, but it will typically also co-precipitate other components (e.g. proteins, nucleic acid etc.).

Precipitated Vi may be collected by centrifugation prior to solubilisation.

After precipitation, Vi (typically in the form of a complex with the cationic detergent) is re-solubilised. It is preferred to use a solvent which is relatively selective for Vi in order to minimise contaminants (e.g. proteins, nucleic acid etc.). Ethanol has been found to be advantageous in this respect, and it is highly selective for the CTAB-Vi complex. Other lower alcohols may be used (e.g. methanol, propan-1-ol, propan-2-ol, butan-1-ol, butan-2-ol, 2-methyl-propan-1-ol, 2-methyl-propan-2-al, diols etc.)

The alcohol is preferably added to the precipitated Vi to give a final alcohol concentration (based on total content of alcohol and water) of between 50% and 99% (e.g. around 55%, 60%, 65%, 70%, 75%, 80%, 85%, or around 90%), and preferably between 75% and 95%.

The alcohol may be added to the precipitated Vi in pure form or may be added in a form diluted with a miscible solvent (e.g. water). Preferred solvent mixtures are alcohol: water mixtures, with a preferred ratio of between around 70:30 and around 95:5 (e.g. 75:25, 80:20, 85:15, 90:10).

Compared with conventional processes for preparing capsular polysaccharides, the two-step process of precipitation followed by alcohol extraction is quicker and simpler.

In contrast to the process described in ref 17, the process uses cationic detergent rather than anionic detergent. Unlike the process of ref 18, precipitation does not require an inert porous support.

Furthermore, unlike prior art processes, an alcohol is used to re-solubilise Vi rather than to precipitate it.

Further Processing of the Solubilised Polysaccharide

After re-solubilisation, Vi is further treated to remove contaminants because, in human vaccine production, even minor contamination is not acceptable.

This treatment may include centrifugation of the solubilised CTAB-Vi complex, followed by precipitation of Vi from the obtained supernatant by exchanging cations (e.g. by the addition of calcium or sodium salts) to give a Vi precipitate that is insoluble in alcohol but soluble in water.

This precipitate may be collected by centrifugation and further washed in alcohol and re-solubilised in an aqueous solution, if desired.

The treatment process will also typically involve one or more steps of filtration.

Depth filtration may be used. This is particularly useful for clarification.

Filtration through activated carbon may be used. This is useful for removing pigments and trace organic compounds. It can be repeated until, for example, $OD_{275\,nm}<0.2$.

Size filtration or ultrafiltration may be used.

If Vi is hydrolysed, the hydrolysate will generally be sized in order to remove short-length oligosaccharides. This can be achieved in various ways, such as ultrafiltration followed by ion-exchange chromatography.

The invention is not limited to saccharides purified from natural sources, however, and the saccharides may be obtained by other methods, such as total or partial synthesis.

Conjugates

Pure Vi is a poor immunogen. For protective efficacy, therefore, Vi may be presented to the immune system as a Vi-carrier conjugate. The use of conjugation to carrier proteins in order to enhance the immunogenicity of carbohydrate antigens is well known [e.g. reviewed in refs. 19 to 27 etc.] and is used in particular for paediatric vaccines [28]. As described above, a saccharide may be conjugated to a carrier protein or to a mixture of different carrier proteins. Similarly, a carrier protein may carry a saccharide or a mixture of different saccharides, i.e. multiple different saccharides [29].

The invention provides a conjugate of (i) Vi, and (ii) $CRM_{197}$ as a carrier protein.

The $CRM_{197}$ may be covalently conjugated to Vi directly or via a linker.

Any suitable conjugation reaction can be used, with any suitable linker where necessary.

Oligosaccharides will typically be sized prior to conjugation. Where the composition of the invention includes a depolymerised saccharide, it is preferred that depolymerisation precedes conjugation.

Attachment of Vi to $CRM_{197}$ is preferably via a —$NH_2$ group e.g. in the side chain of a lysine residue in $CRM_{197}$, or of an arginine residue. Attachment to $CRM_{197}$ may also be via a —SH group e.g. in the side chain of a cysteine residue. Alternatively, Vi may be attached to $CRM_{197}$ via a linker molecule as described below.

Vi will typically be activated or functionalised prior to conjugation. A preferred technique uses carbodiimides (e.g. 1-ethyl-3(3-dimethylaminopropyl)carbodiimide (EDAC)). Other suitable techniques use hydrazides, active esters, norborane, p-nitrobenzoic acid, N-hydroxysuccinimide, S—NHS, EDAC, TSTU (see also the introduction to reference 30).

Linkages via a linker group to carrier proteins in general may be made using any known procedure, for example, the procedures described in references 31 and 32. A useful type of linkage is an adipic acid linker, which may be formed by coupling a free —$NH_2$ group (e.g. introduced to Vi by amination) with adipic acid (using, for example, diimide activation), and then coupling a protein to the resulting saccharide-adipic acid intermediate [23, 33, 34]. Another useful type of linkage is a carbonyl linker, which may be formed by reaction of a free hydroxyl group of a modified Vi with CDI [35, 36] followed by reaction with a protein to form a carbamate linkage. A useful linker is adipic acid dihydrazide ADH [37]. The carrier protein may be derivatised with ADH (for example, by carbodiimide coupling at a carboxylic acid side group) and subsequently attached to Vi [3] (again, for example, by carbodiimide coupling). Other linkers include β-propionamido [38], nitrophenyl-ethylamine [39], haloacyl halides [40], glycosidic linkages [41], 6-aminocaproic acid [42], N-succinimidyl-3-(2-pyridyldithio)-propionate (SPDP) [43], $C_4$ to $C_{12}$ moieties [44], etc. Carbodiimide condensation can also be used [45].

A useful process for linking Vi to $CRM_{197}$ involves the thiolation of Vi with cystamine or cysteamine carbodiimide coupling) and subsequent reaction with $CRM_{197}$ derivatised with SPDP [46].

Another useful process involves the introduction of amino groups into Vi followed by derivatisation with an adipic diester (e.g. adipic acid N-hydroxysuccinimido diester) and reaction with $CRM_{197}$.

A bifunctional linker may be used to provide a first group for coupling to an amine group that has been introduced into Vi and a second group for coupling to the carrier (typically for coupling to an amine in the carrier).

The first group in the bifunctional linker is thus able to react with an amine group (—$NH_2$) on Vi. This reaction will typically involve an electrophilic substitution of the amine's hydrogen. The second group in the bifunctional linker is able to react with an amine group on the carrier. This reaction will again typically involve an electrophilic substitution of the amine.

Where the reactions with both Vi and the carrier protein involve amines then it is preferred to use a bifunctional linker, for example a homobifunctional linker of the formula X-L-X, where: the two X groups are the same as each other and can react with the amines; and where L is a linking moiety in the linker. A useful X group is N-oxysuccinimide. L may have formula L'-$L^2$-L', where L' is carbonyl. Useful $L^2$ groups are straight chain alkyls with 1 to 10 carbon atoms (e.g. $C_1$, $C_2$, $C_3$, $C_4$, $C_5$, $C_6$, $C_7$, $C_8$, $C_9$, $C_{10}$) e.g. —$(CH_2)_4$—.

Other X groups are those which form esters when combined with HO-L-OH, such as norborane, p-nitrobenzoic acid, and sulfo-N-hydroxysuccinimide.

Further bifunctional linkers for use with the invention include acryloyl halides (e.g. chloride) and haloacylhalides.

The linker will generally be added in molar excess to modified Vi.

Preferred carrier proteins are bacterial toxins, such as diphtheria or tetanus toxins, or toxoids or mutants thereof. These are commonly used in conjugate vaccines. The $CRM_{197}$ diphtheria toxin mutant is particularly preferred [47].

Other suitable carrier proteins include the *N. meningitidis* outer membrane protein complex [48], synthetic peptides [49,50], heat shock proteins [51,52], pertussis proteins [53, 54], cytokines [55], lymphokines [55], hormones [55], growth factors [55], artificial proteins comprising multiple human $CD4^+$ T cell epitopes from various pathogen-derived antigens [56] such as N19 [57], protein D from *H. influenzae* [58-60], pneumolysin [61] or its non-toxic derivatives [62], pneumococcal surface protein PspA [63], iron-uptake proteins [64], toxin A or B from *C. difficile* [65], recombinant *Pseudomonas aeruginosa* exoprotein A (rEPA) [66], etc. It is possible to use mixtures of carrier proteins. A single carrier protein may carry multiple Vi saccharides [67].

Conjugates may have excess carrier protein (w/w) or excess Vi (w/w) e.g. in the ratio range of 1:5 to 5:1. Conjugates with excess carrier protein are typical e.g. in the range 0.2:1 to 0.9:1, such as 0.5:1, or with equal weights (1:1). In some embodiments the Vi:protein ratio is between 0.4:1 and 1.2:1.

When the conjugate forms the Vi component in an immunogenic composition of the invention, the composition may also comprise free carrier protein [68].

The Vi moiety in the conjugate is preferably a low molecular weight Vi polysaccharide or an oligosaccharide, as defined above. Oligosaccharides will typically be sized prior to conjugation.

The protein-Vi conjugate is preferably soluble in water and/or in a physiological buffer.

Pharmaceutical Compositions

The invention provides a pharmaceutical composition comprising (a) Vi conjugate, and (b) a pharmaceutically acceptable carrier. A thorough discussion of such carriers is available in ref 69.

Microbial infections affect various areas of the body and so the compositions of the invention may be prepared in various forms. For example, the compositions may be prepared as injectables, either as liquid solutions or suspensions. Solid forms suitable for solution in, or suspension in, liquid vehicles prior to injection can also be prepared. The composition may be prepared for topical administration e.g. as an ointment, cream or powder. The composition be prepared for oral administration e.g. as a tablet or capsule, or as a syrup (optionally flavoured). The composition may be prepared for pulmonary administration e.g. as an inhaler, using a fine powder or a spray. The composition may be prepared as a suppository or pessary. The composition may be prepared for nasal, aural or ocular administration e.g. as drops, as a spray, or as a powder [e.g. 70]. The composition may be included in a mouthwash. The composition may be lyophilised.

The pharmaceutical composition is preferably sterile. It is preferably pyrogen-free. It is preferably buffered e.g. at between pH 6 and pH 8, generally around pH 7.

A composition of the invention may comprise a Vi conjugate and saline.

The invention also provides a delivery device containing a pharmaceutical composition of the invention. The device may be, for example, a syringe or an inhaler.

Pharmaceutical compositions of the invention are preferably immunogenic compositions, in that they comprise an immunologically effective amount of Vi immunogen. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials. A dose of between 1 µg and 20 µg of saccharide is expected e.g. about 5 µg/dose. Dosage treatment may be a single dose schedule or a multiple close schedule (e.g. including booster doses). The composition may be administered in conjunction with other immunoregulatory agents.

Once formulated, the compositions of the invention can be administered directly to the subject. The subjects to be treated can be animals; in particular, human subjects can be treated.

Immunogenic compositions of the invention may be used therapeutically (i.e. to treat an existing infection) or prophylactically (i.e. to prevent future infection).

An immunogenic composition may be unadjuvanted. In other embodiments, though, an immunogenic composition may include an adjuvant, which can function to enhance the immune responses (humoral and/or cellular) elicited in a patient who receives the composition. Adjuvants that can be used with the invention include, but are not limited to:

A mineral-containing composition, including calcium salts and aluminum salts (or mixtures thereof). Calcium salts include calcium phosphate (e.g. the "CAP" particles disclosed in ref. 71). Aluminum salts include hydroxides, phosphates, sulfates, etc., with the salts taking any suitable form (e.g. gel, crystalline, amorphous, etc.). Adsorption to these salts is preferred. The mineral containing compositions may also be formulated as a particle of metal salt [72]. The adjuvants known as aluminum hydroxide and aluminum phosphate may be used. These names are conventional, but are used for convenience only, as neither is a precise description of the actual chemical compound which is present (e.g. see chapter 9 of reference 155). The invention can use any of the "hydroxide" or "phosphate" adjuvants that are in general use as adjuvants. The adjuvants known as "aluminium hydroxide" are typically aluminium oxyhydroxide salts, which are usually at least partially crystalline. The adjuvants known as "aluminium phosphate" are typically aluminium hydroxyphosphates, often also containing a small amount of sulfate (i.e. aluminium hydroxyphosphate sulfate). They may be obtained by precipitation, and the reaction conditions and concentrations during precipitation influence the degree of substitution of phosphate for hydroxyl in the salt. The invention can use a mixture of both an aluminium hydroxide and an aluminium phosphate. In this case there may be more aluminium phosphate than hydroxide e.g. a weight ratio of at least 2:1 e.g. ≥5:1, ≥6:1, ≥7:1, ≥8:1, ≥9:1, etc. The concentration of $Al^{+++}$ in a composition for administration to a patient is preferably less than 10 mg/ml e.g. ≤5 mg/ml, ≤4 mg/ml, ≤3 mg/ml, ≤2 mg/ml, ≤1 mg/ml, etc. A preferred range is between 0.3 and 1 mg/ml. A maximum of 0.85 mg/dose is preferred.

Saponins [chapter 22 of ref. 155], which are a heterologous group of sterol glycosides and triterpenoid glycosides that are found in the bark, leaves, stems, roots and even flowers of a wide range of plant species. Saponin from the bark of the *Quillaia saponaria* Molina tree have been widely studied as adjuvants. Saponin can also be commercially obtained from *Smilax ornata* (sarsaprilla), *Gypsophilla paniculata* (brides veil), and *Saponaria officianalis* (soap root). Saponin adjuvant formulations include purified formulations, such as QS21, as well as lipid formulations, such as ISCOMs. QS21 is marketed as Stimulon™. Saponin compositions have been purified using HPLC and RP-HPLC. Specific purified fractions using these techniques have been identified, including QS7, QS17, QS18, QS21, QH-A, QH-B and QH-C. Preferably, the saponin is QS21. A method of production of QS21 is disclosed in ref. 73. Saponin formulations may also comprise a sterol, such as cholesterol [74]. Combinations of saponins and cholesterols can be used to form unique particles called immunostimulating complexes (ISCOMs) [chapter 23 of ref. 155]. ISCOMs typically also include a phospholipid such as phosphatidylethanolamine or phosphatidylcholine. Any known saponin can be used in ISCOMs. Preferably, the ISCOM includes one or more of QuilA, QHA & QHC. ISCOMs are further described in refs. 74-76. Optionally, the ISCOMS may be devoid of additional detergent [77]. A review of the development of saponin based adjuvants can be found in refs. 78 & 79.

Bacterial ADP-ribosylating toxins (e.g. the *E. coli* heat labile enterotoxin "LT", cholera toxin "CT", or pertussis toxin "PT") and detoxified derivatives thereof, such as the mutant toxins known as LT-K63 and LT-R72 [80]. The use of detoxified ADP-ribosylating toxins as mucosal adjuvants is described in ref. 81 and as parenteral adjuvants in ref 82.

Bioadhesives and mucoadhesives, such as esterified hyaluronic acid microspheres [83] or chitosan and its derivatives [84].

Microparticles (i.e. a particle of ~100 nm to ~150 µm in diameter, more preferably ~200 nm to ~30 µm in diameter, or ~500 nm to ~10 µm in diameter) formed from materials that are biodegradable and non-toxic (e.g. a poly(α-hydroxy acid), a polyhydroxybutyric acid, a polyorthoester, a polyanhydride, a polycaprolactone, etc.), with poly(lactide-co-glycolide) being preferred, optionally treated to have a negatively-charged surface (e.g. with SDS) or a positively-charged surface (e.g. with a cationic detergent, such as CTAB).

Liposomes (Chapters 13 & 14 of ref 155). Examples of liposome formulations suitable for use as adjuvants are described in refs. 85-87.

Muramyl peptides, such as N-acetylmuramyl-L-threonyl-D-isoglutamine ("thr-MDP"), N-acetyl-normuramyl-L-alanyl-D-isoglutamine (nor-MDP), N-acetylglucsaminyl-N-acetylmuramyl-L-Al-D-isoglu-L-Ala-dipalmitoxy propylamide ("DTP-DPP", or "Theramide™"), N-acetylmuramyl-L-alanyl-D-isoglutaminyl-L-alanine-2-(1'-2'dipalmitoyl-sn-glycero-3-hydroxyphosphotyloxy)-ethylamine ("MTP-PE").

A polyoxidonium polymer [88,89] or other N-oxidized polyethylene-piperazine derivative.

A CD1d ligand, such as an α-glycosylceramide [90-97] (e.g. α-galactosylceramide), phytosphingosine-containing α-glycosylceramides, OCH, KRN7000 [(2S,3S,4R)-1-O-(α-D-galactopyranosyl)-2-(N-hexacosanoylamino)-1,3,4-octadecanetriol], CRONY-101, 3"-O-sulfo-galactosylceramide, etc.

A gamma inulin [98] or derivative thereof, such as algammulin.

An oil-in-water emulsion. Various such emulsions are known, and they typically include at least one oil and at least one surfactant, with the oil(s) and surfactant(s) being biodegradable (metabolisable) and biocompatible. The oil droplets in the emulsion are generally less than 5 µm in diameter, and may even have a sub-micron diameter, with these small sizes being achieved with a microfluidiser to provide stable emulsions. Droplets with a size less than 220 nm are preferred as they can be subjected to filter sterilization.

An immunostimulatory oligonucleotide, such as one containing a CpG motif (a dinucleotide sequence containing an unmethylated cytosine residue linked by a phosphate bond to a guanosine residue), or a CpI motif (a dinucleotide sequence containing cytosine linked to inosine), or a double-stranded RNA, or an oligonucleotide containing a palindromic sequence, or an oligonucleotide containing a poly(dG) sequence. Immunostimulatory oligonucleotides can include nucleotide modifications/analogs such as phosphorothioate modifications and can be double-stranded or (except for RNA) single-stranded. References 99, 100 and 101 disclose possible analog substitutions e.g. replacement of guanosine with 2'-deoxy-7-deazaguanosine. The adjuvant effect of CpG oligonucleotides is further discussed in refs. 102-107. A CpG sequence may be directed to TLR9, such as the motif GTCGTT or TTCGTT [108]. The CpG sequence may be specific for inducing a Th1 immune response, such as a CpG-A ODN (oligodeoxynucleotide), or it may be more specific for inducing a B cell response, such a CpG-B ODN. CpG-A and CpG-B ODNs are discussed in refs. 109-111. Preferably, the CpG is a CpG-A ODN. Preferably, the CpG oligonucleotide is constructed so that the 5' end is accessible for receptor recognition. Optionally, two CpG oligonucleotide sequences may be attached at their 3' ends to form "immunomers". See, for example, references 108 & 112-114. A useful CpG adjuvant is CpG7909, also known as ProMune™ (Coley Pharmaceutical Group, Inc.). Another is CpG1826. As an alternative, or in addition, to using CpG sequences, TpG sequences can be used [115], and these oligonucleotides may be free from unmethylated CpG motifs. The immunostimulatory oligonucleotide may be pyrimidine-rich. For example, it may comprise more than one consecutive thymidine nucleotide (e.g. TTTT, as disclosed in ref 115), and/or it may have a nucleotide composition with >25% thymidine (e.g. >35%, >40%, >50%, >60%, >80%, etc.). For example, it may comprise more than one consecutive cytosine nucleotide (e.g. CCCC, as disclosed in ref. 115), and/or it may have a nucleotide composition with >25% cytosine (e.g. >35%, >40%, >50%, >60%, >80%, etc.). These oligonucleotides may be free from unmethylated CpG motifs. Immunostimulatory oligonucleotides will typically comprise at least 20 nucleotides. They may comprise fewer than 100 nucleotides.

A particularly useful adjuvant based around immunostimulatory oligonucleotides is known as IC31™ [161]. Thus an adjuvant used with the invention may comprise a mixture of (i) an oligonucleotide (e.g. between 15-40 nucleotides) including at least one (and preferably multiple) CpI motifs, and (ii) a polycationic polymer, such as an oligopeptide (e.g. between 5-20 amino acids) including at least one (and preferably multiple) Lys-Arg-Lys tripeptide sequence(s). The oligonucleotide may be a deoxynucleotide comprising 26-mer sequence 5'-(IC)$_{13}$-3'. The polycationic polymer may be a peptide comprising 11-mer amino acid Lys-Leu-Lys-Leu$_5$-Lys-Leu-Lys [SEQ ID NO: 1].

3-O-deacylated monophosphoryl lipid A ('3dMPL', also known as 'MPL™') [117-120]. In aqueous conditions, 3dMPL can form micellar aggregates or particles with different sizes e.g. with a diameter <150 nm or >500 nm. Either or both of these can be used with the invention, and the better particles can be selected by routine assay. Smaller particles (e.g. small enough to give a clear aqueous suspension of 3dMPL) are preferred for use according to the invention because of their superior activity [121]. Preferred particles have a mean diameter less than 220 nm, more preferably less than 200 nm or less than 150 nm or less than 120 nm, and can even have a mean diameter less than 100 nm. In most cases, however, the mean diameter will not be lower than 50 nm.

Methyl inosine 5'-monophosphate ("MIMP") [122].

A polyhydroxylated pyrrolizidine compound [123], such as one having formula:

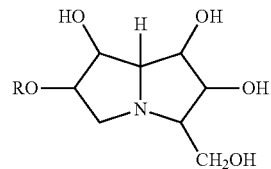

where R is selected from the group comprising hydrogen, straight or branched, unsubstituted or substituted, saturated or unsaturated acyl, alkyl (e.g. cycloalkyl), alkenyl, alkynyl and aryl groups, or a pharmaceutically acceptable salt or derivative thereof. Examples include, but are not limited to: casuarine, casuarine-6-α-D-glucopyranose, 3-epi-casuarine, 7-epi-casuarine, 3,7-diepi-casuarine, etc.

An imidazoquinoline compound, such as Imiquimod ("R-837") [124,125], Resiquimod ("R-848") [126], and their analogs; and salts thereof (e.g. the hydrochloride salts). Further details about immunostimulatory imidazoquinolines can be found in references 127 to 131.

A thiosemicarbazone compound, such as those disclosed in reference 132. Methods of formulating, manufacturing, and screening for active compounds are also described in reference 132. The thiosemicarbazones are particularly effective in the stimulation of human peripheral blood mononuclear cells for the production of cytokines, such as TNF-α.

A tryptanthrin compound, such as those disclosed in reference 133. Methods of formulating, manufacturing, and screening for active compounds are also described in reference 133. The thiosemicarbazones are particularly effective in the stimulation of human peripheral blood mononuclear cells for the production of cytokines, such as TNF-α.

A nucleoside analog, such as: (a) Isatorabine (ANA-245; 7-thia-8-oxoguanosine):

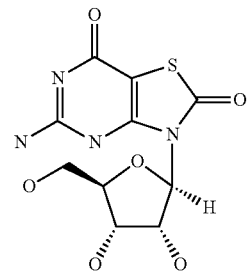 [SMILES: Nc1nc(=O)c2sc(=O)n([C@@H]3O[C@H](CO)[C@@H](O)[C@H]3O)c2[nH]1]

and prodrugs thereof; (b) ANA975; (c) ANA-025-1; (d) ANA380; (e) the compounds disclosed in references 134 to 136Loxoribine (7-allyl-8-oxoguanosine) [137].

Compounds disclosed in reference 138, including: Acylpiperazine compounds, Indoledione compounds, Tetrahydraisoquinoline (THIQ) compounds, Benzocyclodione compounds, Aminoazavinyl compounds, Aminobenzimidazole quinolinone (ABIQ) compounds [139,140], Hydrapthalamide compounds, Benzophenone compounds, Isoxazole compounds, Sterol compounds, Quinazilinone compounds, Pyrrole compounds [141], Anthraquinone compounds, Quinoxaline compounds, Triazine compounds, Pyrazalopyrimidine compounds, and Benzazole compounds [142].

An aminoalkyl glucosaminide phosphate derivative, such as RC-529 [143,144].
A phosphazene, such as poly[di(carboxylatophenoxy) phosphazene] ("PCPP") as described, for example, in references 145 and 146.
A compound of formula I, II or III, or a salt thereof:
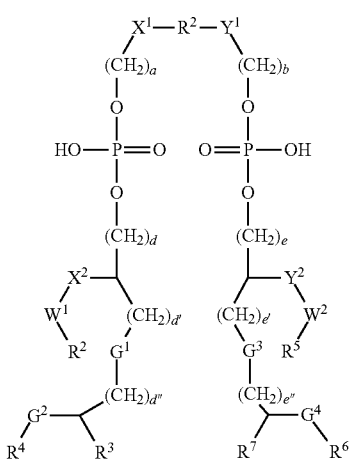
I
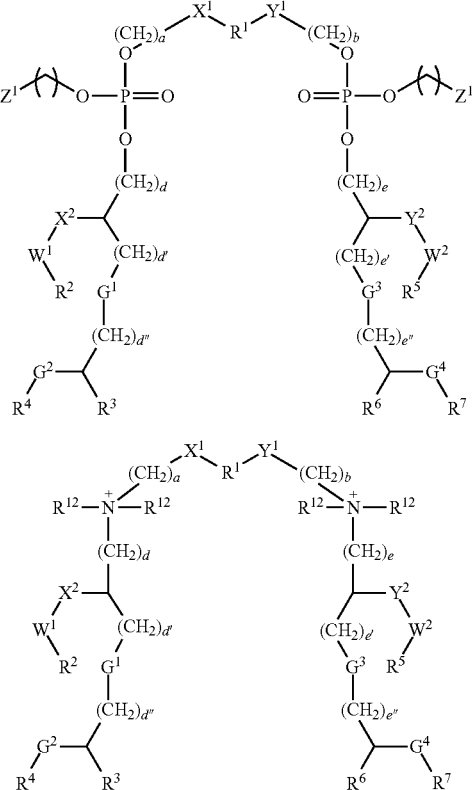
II
III
as defined in reference 1147, such as 'ER 803058', 'ER 803732', 'ER 804053', ER 804058, 'ER 804059', 'ER 804442', 'ER 804680', 'ER 804764', ER 803022 or 'ER 804057' e.g.:
ER804057
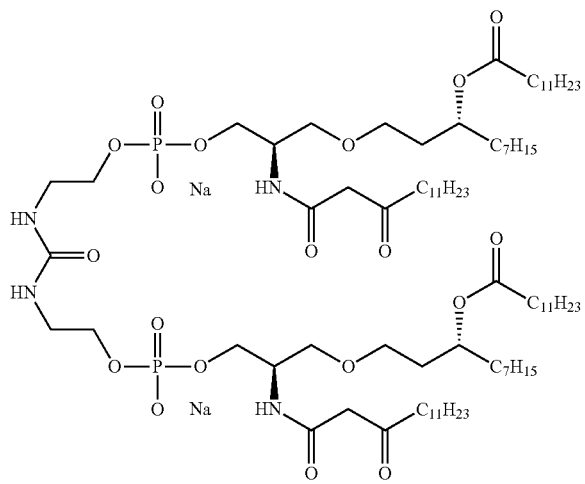

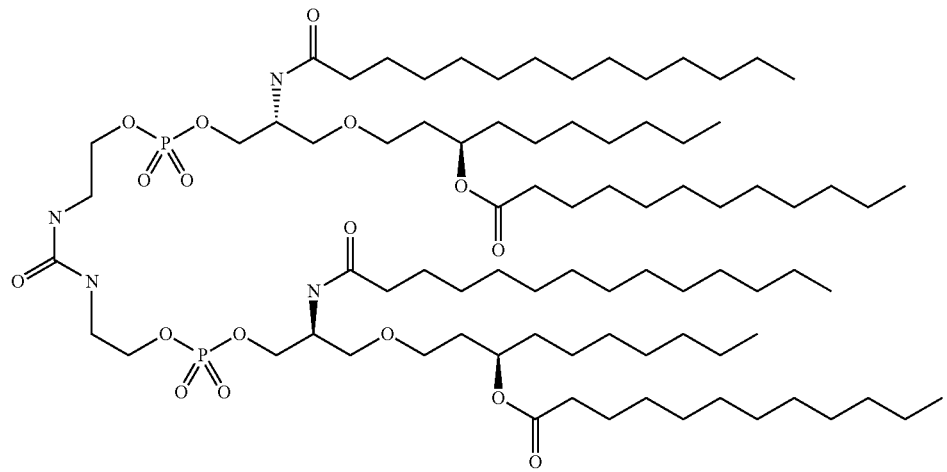

Derivatives of lipid A from *Escherichia coli* such as OM-174 (described in refs. 148 & 149).

Compounds containing lipids linked to a phosphate-containing acyclic backbone, such as the TLR4 antagonist E5564 [150,151]:

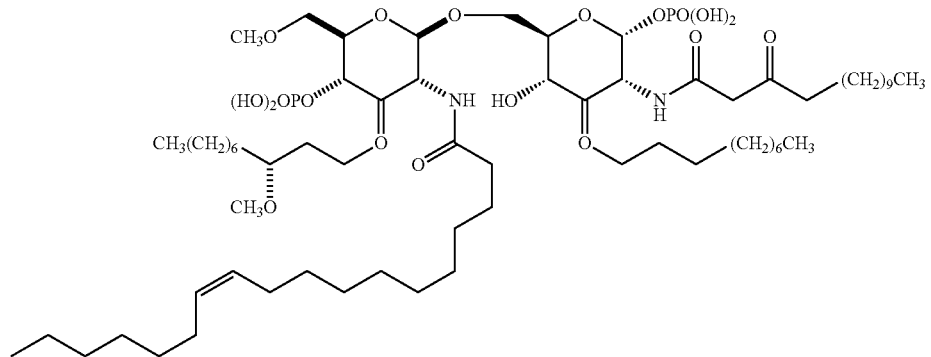

These and other adjuvant-active substances are discussed in more detail in references 155 & 156.

Antigens and adjuvants in a composition will typically be in admixture.

Compositions may include two or more of said adjuvants. For example, they may advantageously include both an oil-in-water emulsion and 3dMPL, etc.

Specific oil-in-water emulsion adjuvants useful with the invention include, but are not limited to:

A submicron emulsion of squalene, TWEEN 80, and SPAN 85. The composition of the emulsion by volume can be about 5% squalene, about 0.5% polysorbate 80 and about 0.5% SPAN 85. In weight terms, these ratios become 4.3% squalene, 0.5% polysorbate 80 and 0.48% SPAN 85. This adjuvant is known as 'MF59' [152-154], as described in more detail in Chapter 10 of ref. 155 and chapter 12 of ref. 156. The MF59 emulsion advantageously includes citrate ions e.g. 10 mM sodium citrate buffer.

An emulsion of squalene, a tocopherol, and TWEEN 80. The emulsion may include phosphate buffered saline. It may also include SPAN 85 (e.g. at 1%) and/or lecithin. These emulsions may have from 2 to 10% squalene, from 2 to 10% tocopherol and from 0.3 to 3% TWEEN 80, and the weight ratio of squalene:tocopherol is preferably ≤1 as this provides a more stable emulsion. Squalene and TWEEN 80 may be present volume ratio of about 5:2. One such emulsion can be made by dissolving TWEEN 80 in PBS to give a 2% solution, then mixing 90 ml of this solution with a mixture of (5 g of DL-α-tocopherol and 5 ml squalene), then microfluidising the mixture. The resulting emulsion may have submicron oil droplets e.g. with an average diameter of between 100 and 250 nm, preferably about 180 nm.

An emulsion of squalene, a tocopherol, and a TRITON detergent (e.g. TRITON X-100). The emulsion may also include a 3d-MPL (see below). The emulsion may contain a phosphate buffer.

An emulsion comprising a polysorbate (e.g. polysorbate 80), a TRITON detergent (e.g. TRITON X-100) and a tocopherol (e.g. an α-tocopherol succinate). The emulsion may include these three components at a mass ratio of about 75:11:10 (e.g. 750 μg/ml polysorbate 80, 110 μg/ml TRITON X-100 and 100 μg/ml α-tocopherol succinate), and these concentrations should include any contribution of these components from antigens. The emulsion may also include squalene. The emulsion may also include a 3d-MPL (see below). The aqueous phase may contain a phosphate buffer.

An emulsion of squalane, polysorbate 80 and poloxamer 401 ("Pluronic™ L121"). The emulsion can be formulated in phosphate buffered saline, pH 7.4. This emulsion is a useful delivery vehicle for muramyl dipeptides, and has been used with threonyl-MDP in the "SAF-1" adjuvant [157] (0.05-1% Thr-MDP, 5% squalane, 2.5% PLURONIC L121 and 0.2% polysorbate 80). It can also be used without the Thr-MDP, as in the "AF" adjuvant [158] (5% squalane, 1.25% PLURONIC L121 and 0.2% polysorbate 80). Microfluidisation is preferred.

An emulsion having from 0.5-50% of an oil, 0.1-10% of a phospholipid, and 0.05-5% of a non-ionic surfactant. As described in reference 159, preferred phospholipid components are phosphatidylcholine, phosphatidylethanolamine, phosphatidylserine, phosphatidylinositol, phosphatidylglycerol, phosphatidic acid, sphingomyelin and cardiolipin. Submicron droplet sizes are advantageous.

A submicron oil-in-water emulsion of a non-metabolisable oil (such as light mineral oil) and at least one surfactant (such as lecithin, TWEEN 80 or SPAN 80). Additives may be included, such as QuilA™ saponin, cholesterol, a saponin-lipophile conjugate (such as GPI-0100, described in reference 160, produced by addition of aliphatic amine to desacylsaponin via the carboxyl group of glucuronic acid), dimethyidioctadecylammonium bromide and/or N,N-dioctadecyl-N, N-bis (2-hydroxyethyl)propanediamine.

An emulsion in which a saponin (e.g. QuilA™ or QS-211 and a sterol (e.g. a cholesterol) are associated as helical micelles [161].

Medical Treatments and Uses

The invention also provides a Vi conjugate of the invention, for use in medicine e.g. for use in raising an antibody response in a mammal.

The invention also provides a method for raising an immune response in a mammal, comprising administering a Vi conjugate or pharmaceutical composition of the invention to the mammal.

The invention also provides the use of a Vi conjugate of the invention in the manufacture of a medicament for preventing or treating typhoid fever in a mammal.

The immune response raised by these methods and uses will generally include an antibody response, preferably a protective antibody response. Methods for assessing antibody responses after saccharide immunisation are well known in the art. The antibody response is preferably an IgA or IgG response. The immune response may be prophylactic and/or therapeutic. The mammal is preferably a human.

Compositions of the invention will generally be administered directly to a patient. Direct delivery may be accomplished by parenteral injection (e.g. subcutaneously, intraperitoneally, intravenously, intramuscularly, or to the interstitial space of a tissue), or by rectal, oral, vaginal, topical, transdermal, intradermal, ocular, nasal, aural, or pulmonary administration. Injection or intranasal administration is preferred.

The invention may be used to elicit systemic and/or mucosal immunity.

Vaccines prepared according to the invention may be used to treat both children (including infants) and adults. Thus a subject may be less than 1 year old, 1-5 years old, 5-15 years old, 15-55 years old, or at least 55 years old. Preferred subjects for receiving the vaccines are the young (e.g. ≤5 years old). The vaccines are not suitable solely for these groups, however, and may be used more generally in a population.

Treatment can be by a single dose schedule or a multiple dose schedule. Multiple doses may be used in a primary immunisation schedule and/or in a booster immunisation schedule. In a multiple dose schedule the various doses may be given by the same or different routes e.g. a parenteral prime and mucosal boost, a mucosal prime and parenteral boost, etc. Administration of more than one dose (typically two doses) is particularly useful in immunologically naïve patients. Multiple doses will typically be administered at least 1 week apart (e.g. about 2 weeks, about 3 weeks, about 4 weeks, about 6 weeks, about 8 weeks, about 10 weeks, about 12 weeks, about 16 weeks, etc.). An example schedule provides a first dose at 6 weeks of age and a second dose at 10 weeks of age, to coincide with existing infant immunisations (co-administration with EPI vaccines). This primary schedule may be followed by a booster dose after a child's first birthday.

Conjugates of the invention may be combined with non-Vi antigens into a single composition for simultaneous immunisation against multiple pathogens. As an alternative to making a combined vaccine, conjugates may be administered to patients at substantially the same time as (e.g. during the same medical consultation or visit to a healthcare professional or vaccination centre) other vaccines. Antigens for use in these combination vaccines or for concomitant administration include, for instance, immunogens from *Streptococcus agalactiae, Staphylococcus aureus* and/or *Pseudomonas aeuruginosa*, hepatitis A virus, hepatitis B virus, *Neisseria meningitidis* (such as saccharides or conjugated saccharides, for serogroups A, C, W135 and/or Y), *Streptococcus pneumoniae* (such as saccharides or conjugated saccharides), etc.

In one embodiment, a composition may comprise a Vi conjugate of the invention in combination with a *Salmonella paratyphi* A antigen, such as an H or O antigen (e.g. an 0:2 saccharide antigen), to provide a bivalent typhoid vaccine. In another embodiment, a composition may comprise a Vi conjugate of the invention in combination with a *Salmonella typhimurium* antigen, such as an H or O antigen (e.g. an 0:9 saccharide). In another embodiment, a composition may comprise a Vi conjugate of the invention in combination with a *Salmonella enteritidis* antigen, such as an H or O antigen (e.g. an O:4,5 saccharide).

DEFINITIONS

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x is optional and means, for example, x±10%.

Where animal (and particularly bovine) materials are used in the culture of cells, they should be obtained from sources that are free from transmissible spongiform encephalopathies (TSEs), and in particular free from bovine spongiform encephalopathy (BSE). Overall, it is preferred to culture cells in the total absence of animal-derived materials.

Where a compound is administered to the body as part of a composition then that compound may alternatively be replaced by a suitable prodrug.

BRIEF DESCRIPTION OF DRAWINGS

FIG. 18 shows the average anti-Vi antibody values.

MODES FOR CARRYING OUT THE INVENTION

Vi Purification

Figure 1:
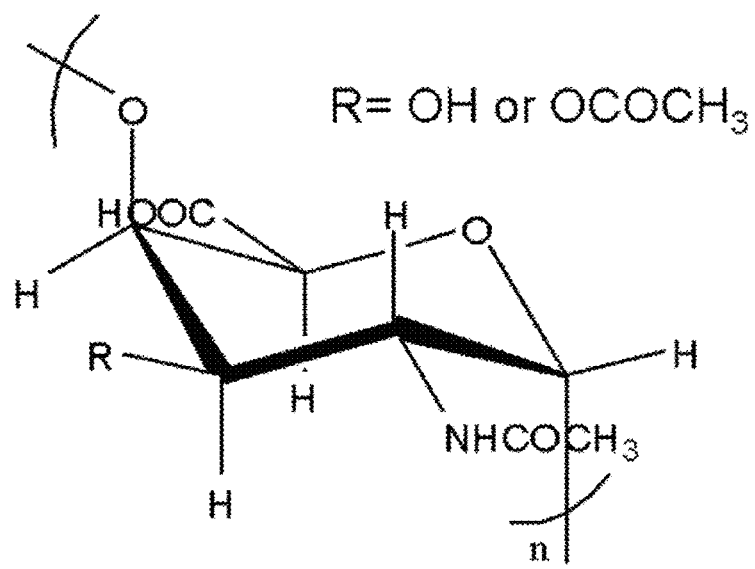
FIG. 1 depicts the structural formula of *S. typhi* Vi (α1,4-N-acetylgalactosaminouronic acid).
Figure 2:
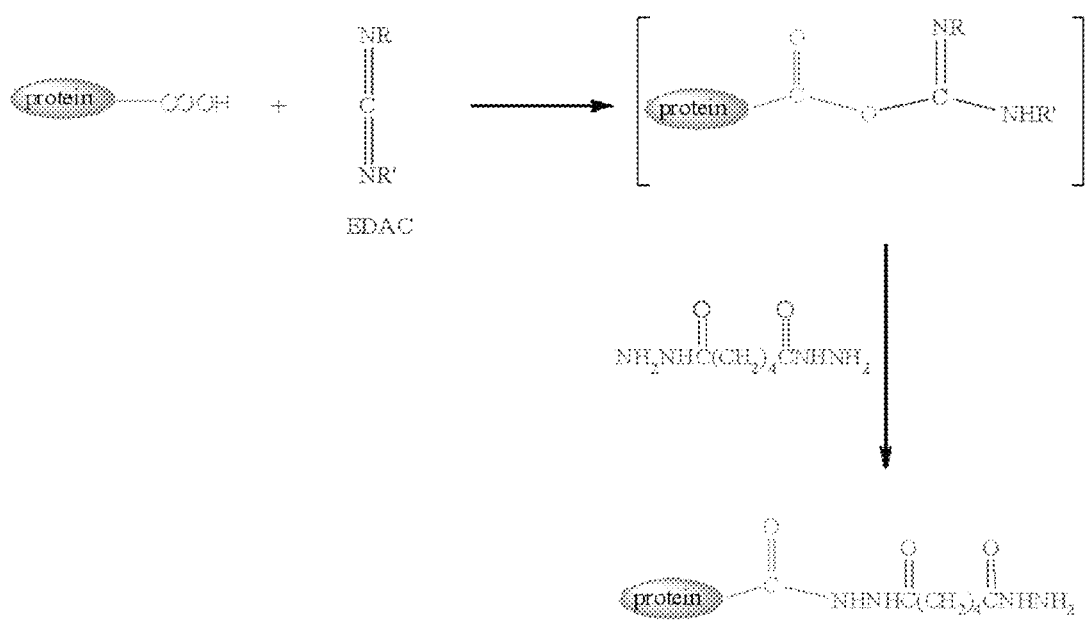
FIG. 2 shows a reaction scheme for the preparation of derivatised proteins.

The supernatant of a 5 L sample of *C. freundii* WR7001 in mod-LB was concentrated (20 times) to 250 ml with a 100K membrane. The sample was diafiltered against NaCl 1 M (2.5 L) and then with water (1.5 L), again with a 100K membrane, and the permeate discarded. A 0.22 µm filter was used to remove turbidity. Subsequently, 0.9% CTAB was added to form a Vi-CTAB precipitate. This was centrifuged at 18000 g for 15 minutes and the supernatant discarded.

The precipitate was suspended in ethanol (96%, 110 ml) and mixed overnight at RT before subsequent centrifugation at 18000 g for 50 minutes, after which the resulting precipitate was discarded. 0.1 M NaCl was added to the supernatant to form a gel which was centrifuged at 18000 g for 10 minutes. The precipitate was collected and washed with ethanol, then solubilised in aqueous NaCl (1 M, 50 ml) and filtered. The retentate was brought to 80% ethanol and centrifuged at 18000 g for 10 minutes. The precipitate was again washed with ethanol. One part of the precipitate remained in suspension (Lot A). The two parts were collected separately as Lot A (97 mg) and Lot B (170 mg).

In a modified process, the supernatant was concentrated to 8.0-10.0 g/L with a 100K membrane. The sample was diafiltered against NaCl 1 M, Tris 0.1M, EDTA 0.02M pH 7.3 (2.5 L) and then with water (2.5 L), again with a 100K membrane, and the permeate was discarded. Subsequently, 2.0% CTAB was added to form a Vi-CTAB precipitate. The precipitate was centrifuged at 18000 g for 15 minutes and the supernatant discarded. The precipitate was then washed with water, centrifuged and resuspended in ethanol (85%) and mixed until completely solubilised. The solution was passed through SP10 and carbon filters. The filtrate was precipitated with NaCl 0.2 M and centrifuged at 18000 g for 5 minutes. The precipitate was resuspended in NaCl 1.0 M to give a concentration of 3-5 mg/mL. This solution was diafiltrated against water and 0.22 µM filtered.

The purification process has a good yield and provides saccharide with good purity (less than 0.5% protein, less than 0.01% nucleic acid) and is gentle enough to preserve high levels of O-acetylation.

Tetanus Toxoid Derivatisation

ADH (3.25 per mg of protein) and 1-ethyl-3-(3-dimethylaminopropyl)carbodiimide-hydrochloride (EDAC) (EDAC/protein=0.152 w/w) were added to tetanus toxoid (in 2-(N-morpholino)ethanesulfonic acid (MES) buffer 50-100 mM, pH 6.18 to 6.20). The reaction was carried out for 1 hour at room temperature.

The reaction mixture was dialysed against 0.2 M NaCl, 5 mM MES buffer, pH 7.05, 2-8° C. and 5 mM MES buffer, pH 7.00, 2-8° C. Derivatised tetanus toxoid (86% yield) was obtained.

CRM$_{197}$ Derivatisation

ADH (3.5 mg per mg of protein) and EDAC (EDAC/protein=0.15 w/w) were added to CRM$_{197}$ (11.5 mg/ml in MES buffer 50-100 mM, pH 6.0). The reaction was carried out for 1 hour at room temperature, pH 6.0-6.2. Maintenance of the pH in this range prevented protein precipitation.

The reaction mixture was dialyzed overnight against 5 mM MES buffer, NaCl 0.2 M, pH 7.0 and then against 5 mM MES buffer, pH 7.0 at 4° C. Protein was measured by microBCA analysis (yield of 75-85%). Sucrose 10% w/v was added to the product and it was stored at −20° C. Rather than store with sucrose, though, it can be stored in 5 mM MES, pH 7.0.

Derivatised Protein Characterisation

Derivatisation of the proteins with ADH was verified by a colorimetric method (TNBS method).

The molar ratio of ADH to TT was measured by MS Maldi-Tof as about 11.

The molar ratio of ADH to CRM$_{197}$ was measured by MS Q-Tof. This showed the formation of several products characterised by the presence of a different number of linkers bound to the protein (from 3 to 10, the principal product containing 6 bound linkers).

The derivatised proteins (and, subsequently, the conjugates) were examined by sodium dodecyl sulfate-polyacrylamide gel electrophoresis (SDS-PAGE) using 3-8% trisacetate gels (NuPAGE). The samples (5-20 µl to have a protein content of 5 µg) were added of DTT 0.5M (1/5 v/v) and of NuPAGE LDS Sample Buffer (1/5 v/v). The mixtures were heated at 100° C. for 1 minute and the samples applied to the wells. The gel was subjected to electophoresis at 30 mA in Tris-Acetate SDS Running Buffer (Invitrogen). At the end it was stained with SimplyBlue SafeStain™ (Invitrogen).

Figure 3:
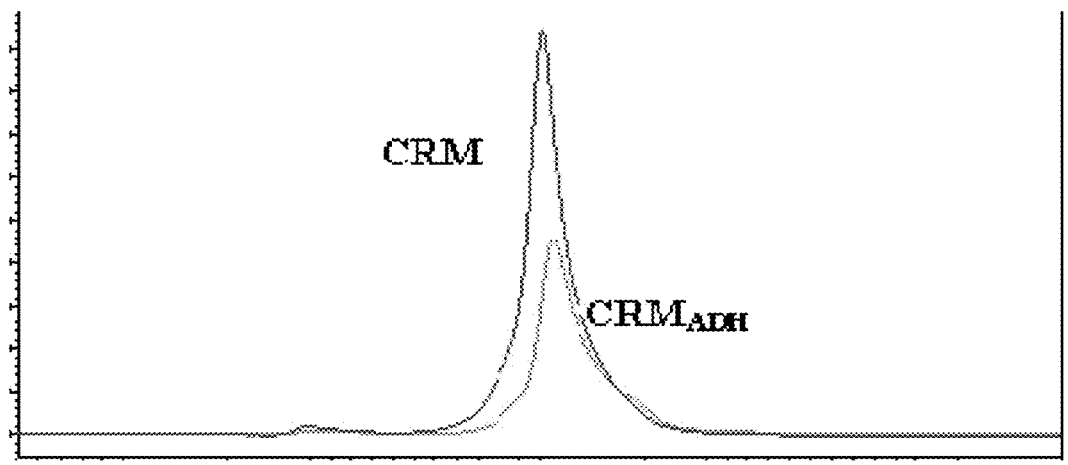
FIG. 3 shows a SEC analysis of $CRM_{197}$ and $CRM_{197}$ derivatised with ADH.
Figure 4:
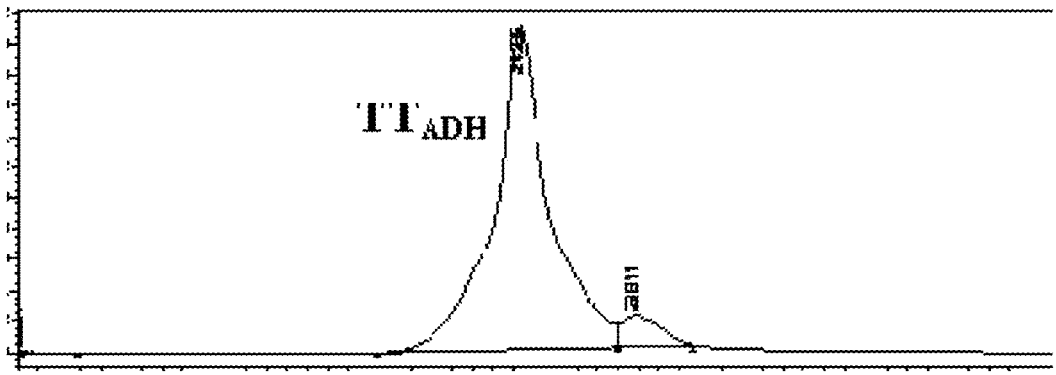
FIG. 4 shows a SEC analysis of tetanus toxoid derivatised with ADH.
Figure 5:
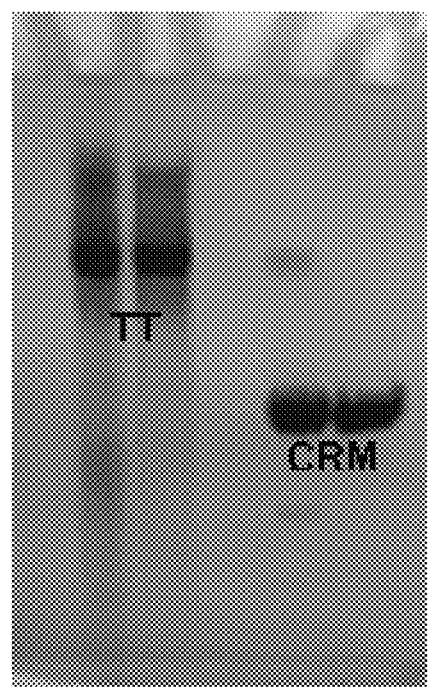
FIG. 5 shows SDS page patterns of, from left to right, TT, $TT_{ADH}$, CRM and $CRM_{ADH}$.
Figure 6:
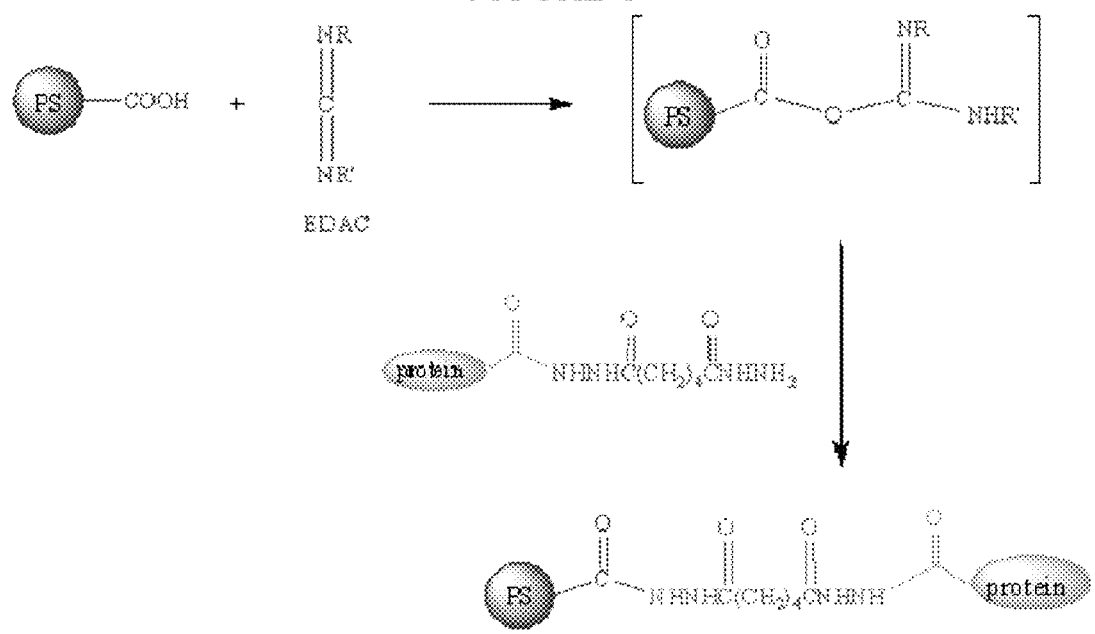
FIG. 6 shows a reaction scheme for the preparation of a Vi-protein conjugate.

SDS-PAGE patterns and SEC profiles (214 nm, TSK gel 4000; phosphate buffer 100 mM+NaCl 100 mM+5% CH$_3$CN, pH 7.0) of the derivatised proteins were found to be similar to those of the native proteins (see FIG. 3 to FIG. 5). Vi Conjugation to Derivatised Tetanus Toxoid EDAC (4.4 mg) was added to Vi (4.6 mg) in a buffered solution at pH 6.08 (1.5 ml 200 mM MES buffer) and allowed to react for 2 minutes at room temperature.

Derivatised tetanus toxoid (9.2 mg) in a buffered solution at pH 7.0 (1.5 ml 5 mM MES buffer) was allowed to react with the activated Vi for 3 hours at room temperature [TT$_{ADH}$]=3.15 mg ml$^{-1}$, [Vi]=1.53 mg ml$^{-1}$, Ratio TT$_{ADH}$/Vi (w)=2, [EDAC]=1.5 mg ml$^{-1}$).

The reaction mixture was dialysed against 0.2 M NaCl, 10 mM phosphate buffer, pH 7.07, 4° C. and purified by SEPHACRYL S-1000 (1.5×90 cm) in 10 mM phosphate buffer, 200 mM NaCl, pH 7.00.

Figure 7:
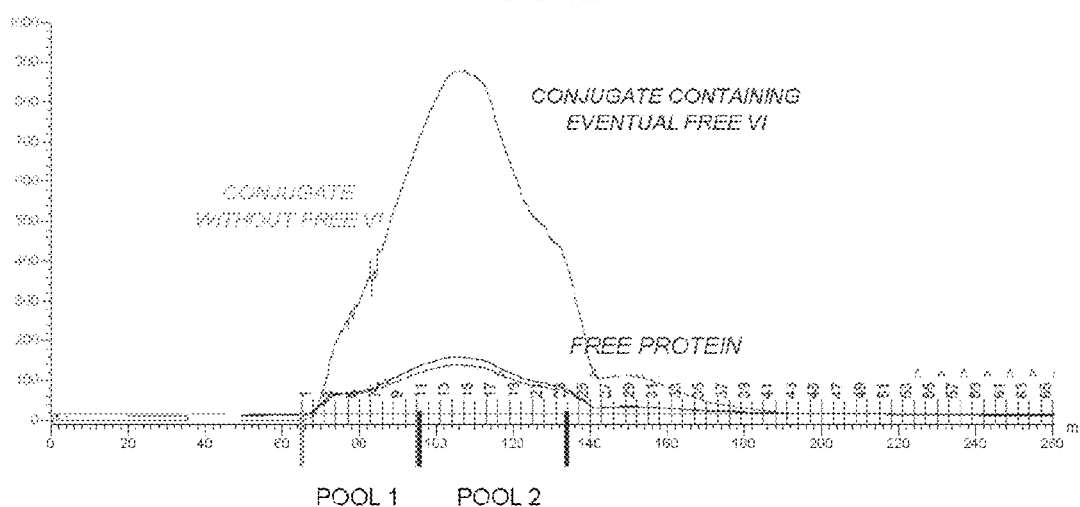
FIG. 7 and FIG. 8 show gel filtration profiles of Vi and tetanus toxoid on SEPHACRYL S-1000.
Figure 8:
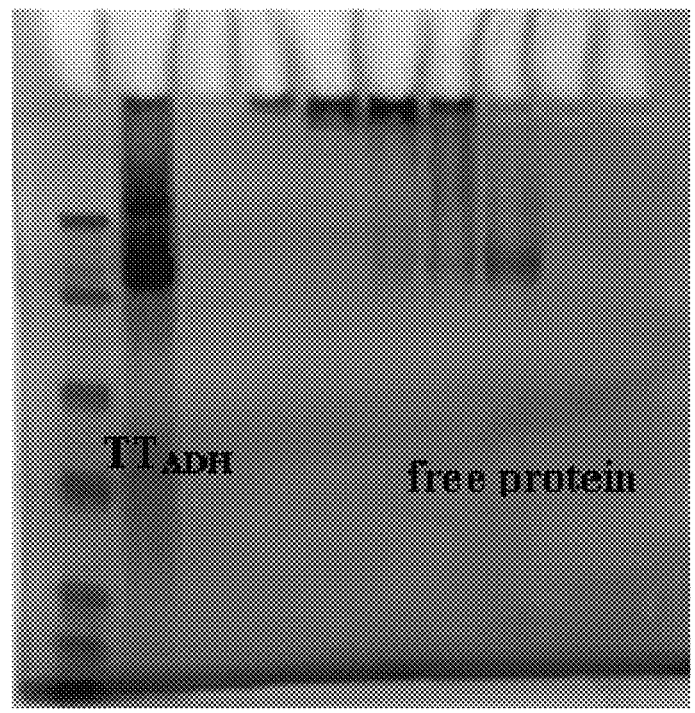

During conjugate purification, two different pools were collected (see FIG. 7), which were characterised by a different MW. Gel filtration profiles of Vi and of TT on SEPHACRYL S-1000 show (see FIG. 7 and FIG. 8):

conjugate purification from the free protein is feasible (pool 1).

conjugate purification from free saccharide is not feasible (pool 2—free Vi co-elutes with the conjugate).

Pool 1 should therefore contain less free Vi than pool 2.

Figure 9:
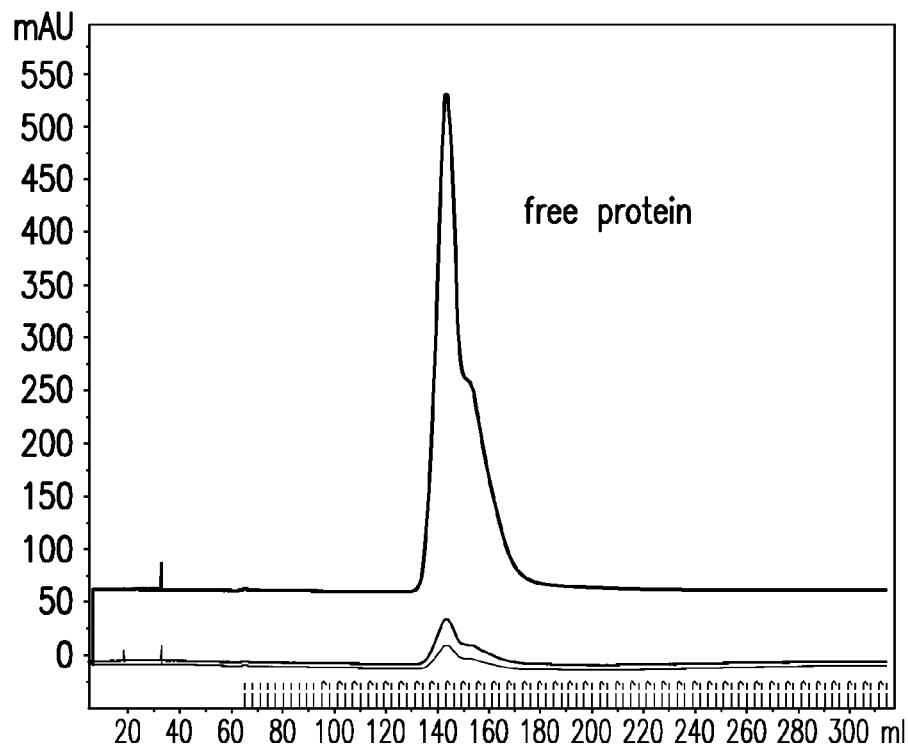
FIG. 9 shows a gel filtration profile of "pool 1"
Figure 10:
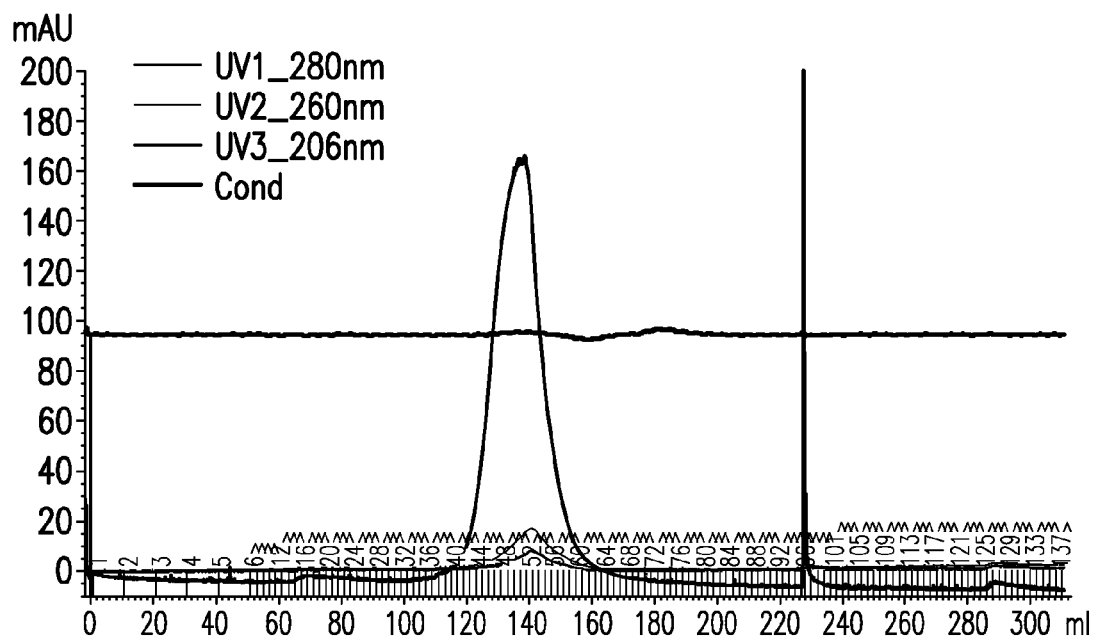
FIG. 10 shows a profile of "pool 2".

FIG. 9 shows the profile on SEPHACRYL S1000 (1.6×90 cm) of the un-conjugated protein with 10 mM phosphate, NaCl 200 mM, pH 7 at a flow of 0.2 ml/min. FIG. 10 shows the profile on SEPHACRYL S1000 (in the same conditions) of free Vi.

Pools 1 and 2 were dialysed against 2 mM phosphate buffer pH 7.0 and their contents were as follows:

| Conjugate Vi-TT$_{ADH}$ | Protein content (micro BCA) | Saccharide content (acridine orange) | Ratio (w/w) saccharide/protein |
|---|---|---|---|
| Pool 1 | 2.46 mg | 1.02 mg | 0.41 |
| Pool 2 | 5.56 mg | 3.73 mg | 0.67 |

Figure 11:
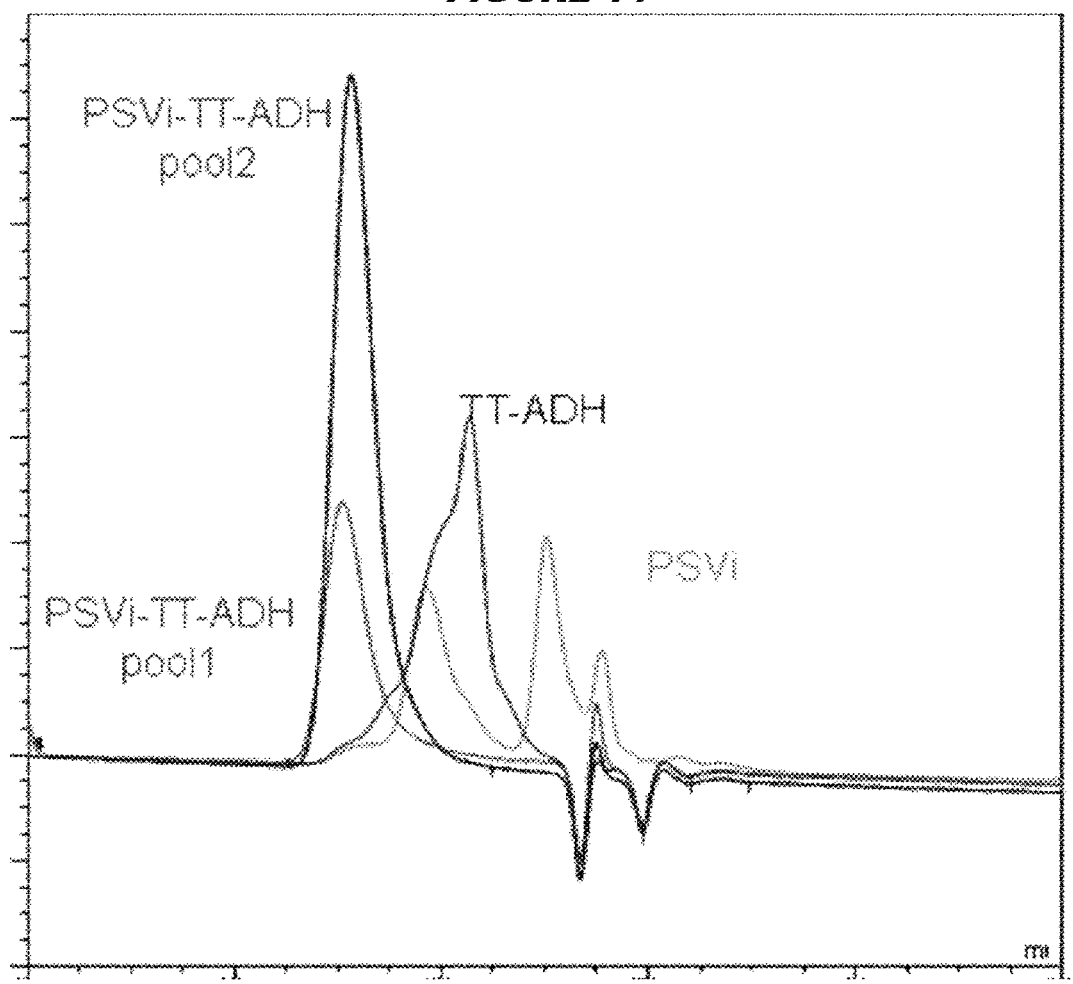
FIG. 11 shows a SEC analysis of Vi–TT$_{ADH}$.
Figure 12:
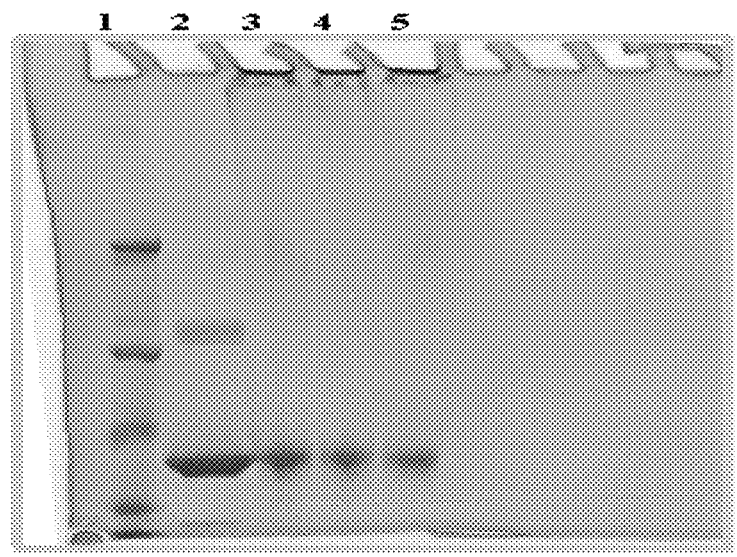
FIG. 12 shows a SDS-PAGE profile (gel 3-8%) of Vi–CRM$_{ADH}$ reaction mixtures after dialysis. Lane 2 is CRM$_{ADH}$ (5 µg), Lanes 3-5 are 10 µl of the reactions mixtures after dialysis of Lots 04-06 respectively.

The conjugate was characterised by SEC analysis (see FIG. 11, 214 nm, TSK gel 6000; phosphate buffer 100 mM+NaCl 100 mM+5% CH$_3$CN, pH 7.0):

PSVi-TT$_{ADH}$ pool 1: polysaccharide 26.8 µg/ml; protein 64.64

(100K or 300K membrane) as follows: reaction mixture diluted from 15 to 50 ml with 10 mM phosphate buffer pH 7.2; membrane: Vivaflow 200 cm$^2$ 100K (regenerated cellulose); P$_{in}$: 1.2-1.3 bar; P$_{out}$: 0.4 bar; flow: 22.4 ml/min; permeate volume: 1.4 L; (28 cycles with 10 mM phosphate buffer pH 7.2); final retentate volume of 152 ml.

The conjugate was characterised by microBCA (protein content), acridine orange titration and NMR/HPAEC-PAD (saccharide content), $^1$H NMR(O-acetyl level and EDAC derivative quantification), HPLC and SDS-PAGE.

Figure 13:
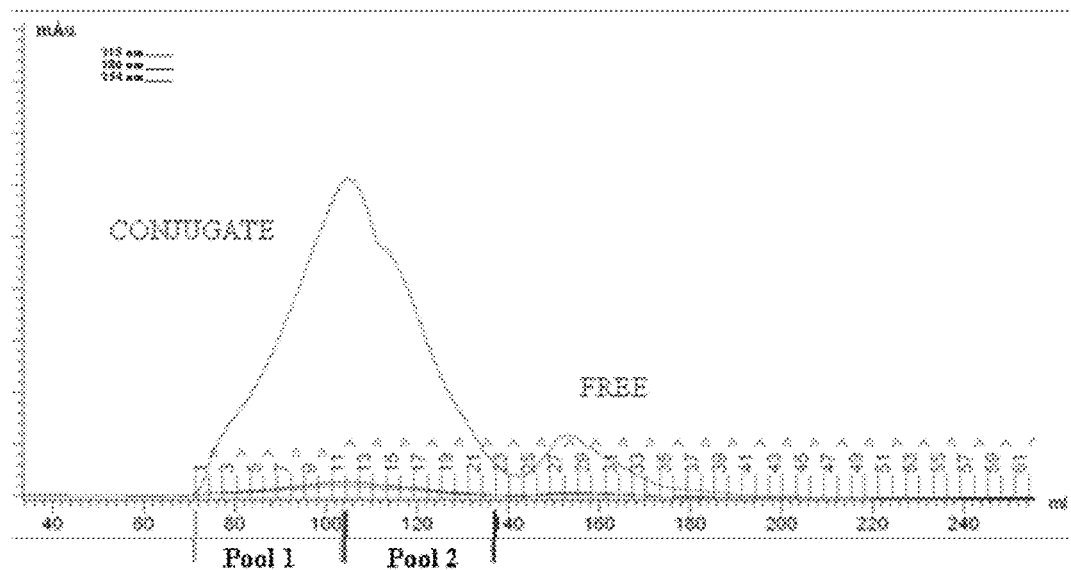
FIG. 13 shows the purification of Lot 06 on SEPHACRYL S-1000.
Figure 14:
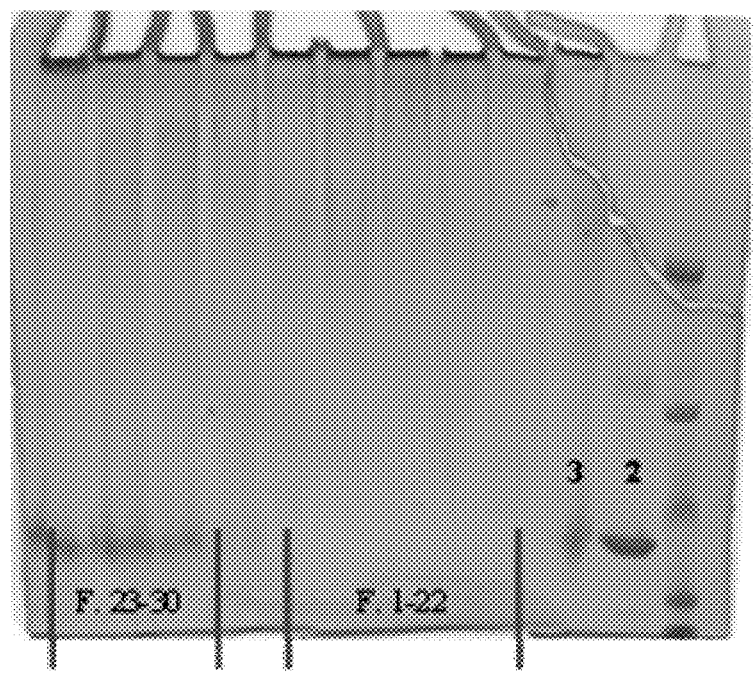
FIG. 14 shows a SDS-PAGE profile (gel 3-8%) of: "2"-CRM$_{ADH}$ 3 µg, "3"-reaction mixture 10 µl and fractions 1-11 and 12-22 of the purification of Lot 06.

FIG. 13 shows the purification of Lot 06 on SEPHACRYL S-1000 (SEPHACRYL S1000 1.6 cm×90 cm; Flow: 0.2 ml/min, Eluent: 200 mM NaCl, 10 mM NaH$_2$PO$_4$, pH 7.0). Fractions (1-11 and 12-22 for Lot 06) were collected for each Lot in two different pools, distinguished by MW. The first pool (earlier fractions) was purified of free saccharide, whilst the second contained an undetermined amount of free saccharide.

The pools were dialyzed against 2 mM NaH$_2$PO$_4$, pH 7.5, at 4° C., overnight and contents were:

| Conjugate | Saccharide conc. (µg/ml) HPAEC-PAD | Saccharide conc. (µg/ml) acridine orange | Protein conc. (µg/ml) | Ratio PS/protein (w/w) HPAEC-PAD or acridine orange | | % yield in protein | % yield in saccharide (HPAEC-PAD) |
|---|---|---|---|---|---|---|---|
| Vi-CRM$_{ADH}$ Lot04 Pool 1 | 24.37 | 32.75 | 52.06 | 0.47 | 0.63 | 64.90 | 84.31 |
| Vi-CRM$_{ADH}$ Lot04 Pool 2 | 78.36 | 59.15 | 106.1 | 0.74 | 0.56 | | |
| Vi-CRM$_{ADH}$ Lot05 Pool 1 | 34.51 | 35.95 | 63.17 | 0.55 | 0.57 | 63.94 | 86.82 |
| Vi-CRM$_{ADH}$ Lot05 Pool 2 | 71.39 | 64.6 | 93.42 | 0.76 | 0.69 | | |
| Vi-CRM$_{ADH}$ Lot06 Pool 1 | 39.12 | 29.55 | 59.1 | 0.66 | 0.5 | 56.89 | 86.23 |
| Vi-CRM$_{ADH}$ Lot06 Pool 2 | 67.73 | 50 | 82.41 | 0.82 | 0.61 | | |

PSVi-TT$_{ADH}$ pool 2: polysaccharide 82.8 µg/ml; protein 123.68 µg/ml
PSVi: 1.4 mg/ml
TT$_{ADH}$: 0.1 mg/ml Vi Conjugation to Derivatised CRM$_{197}$ Three different Vi–CRM$_{ADH}$ Lots ("04", "05", and "06") were prepared as follows:

EDAC (4.4 mg) was added to Vi (4.6 mg, giving a EDAC:Vi molar ratio of about 1.43:1) in a buffered solution at pH 6.0 (1.65 ml 20 mM MES buffer) and mixed for 2 minutes at room temperature. (In later experiments, for comparison, the amount of EDAC was reduced, using molar ratios of 5:1 and 9:1. CRM197 conjugates obtained with these derivatised saccharides were better characterisable and reproducible with <5% of unconjugated CRM-ADH. The ratio 5:1 was better than 1.4:1, and the ratio 9:1 was better than 5:1).

Derivatised CRM$_{197}$ (9.2 mg) in a buffered solution at pH 7.0 (1.085 ml 5 mM MES buffer) was allowed to react with the activated Vi for 3 hours at room temperature ([CRM$_{ADH}$]=3.07 mg ml$^{-1}$, [Vi]=1.53 mg ml$^{-1}$, Ratio CRM$_{ADH}$/Vi (w)=2, [EDAC]=1.47 mg ml$^{-1}$), during which the pH was maintained at 6.0-6.20 by using MES buffer in order to avoid precipitation.

As noted above, CRM$_{ADH}$ is added in 5 mM MES buffer, pH 7. It is necessary that the final mixture is in MES buffer not lower than 50-60 mM at pH 6 to maintain the pH constant during the reaction itself.

The reaction mixture was purified by SEPHACRYL S1000 column (1.5×90 cm) in 10 mM sodium phosphate buffer, 200 mM NaCl, pH 7 at 4° C.

Figure 15:
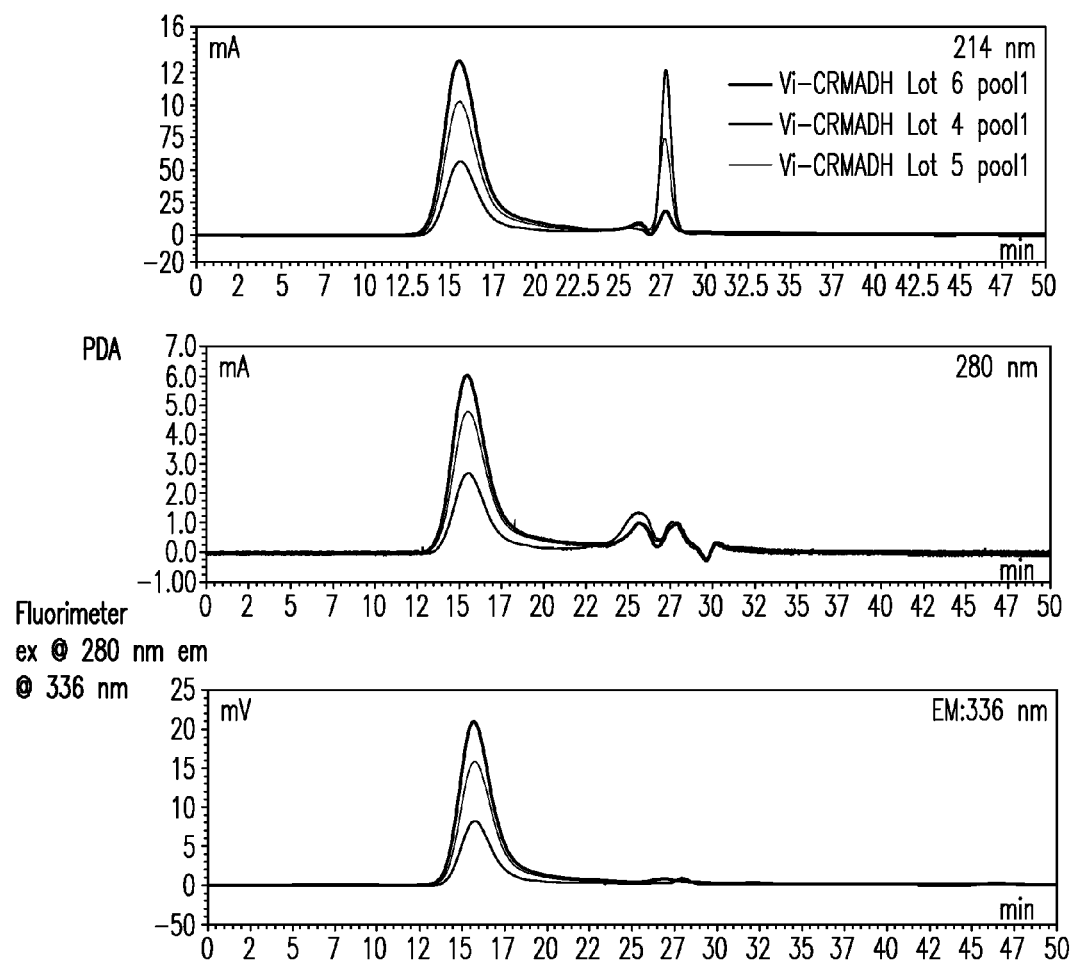
FIGS. 15 to 17 show SEC analyses comparing pools 1 obtained from Lots 04-06, pools 2 obtained from Lots 04-06, and pools 1 and 2 obtained from Lot 06.
Figure 16:
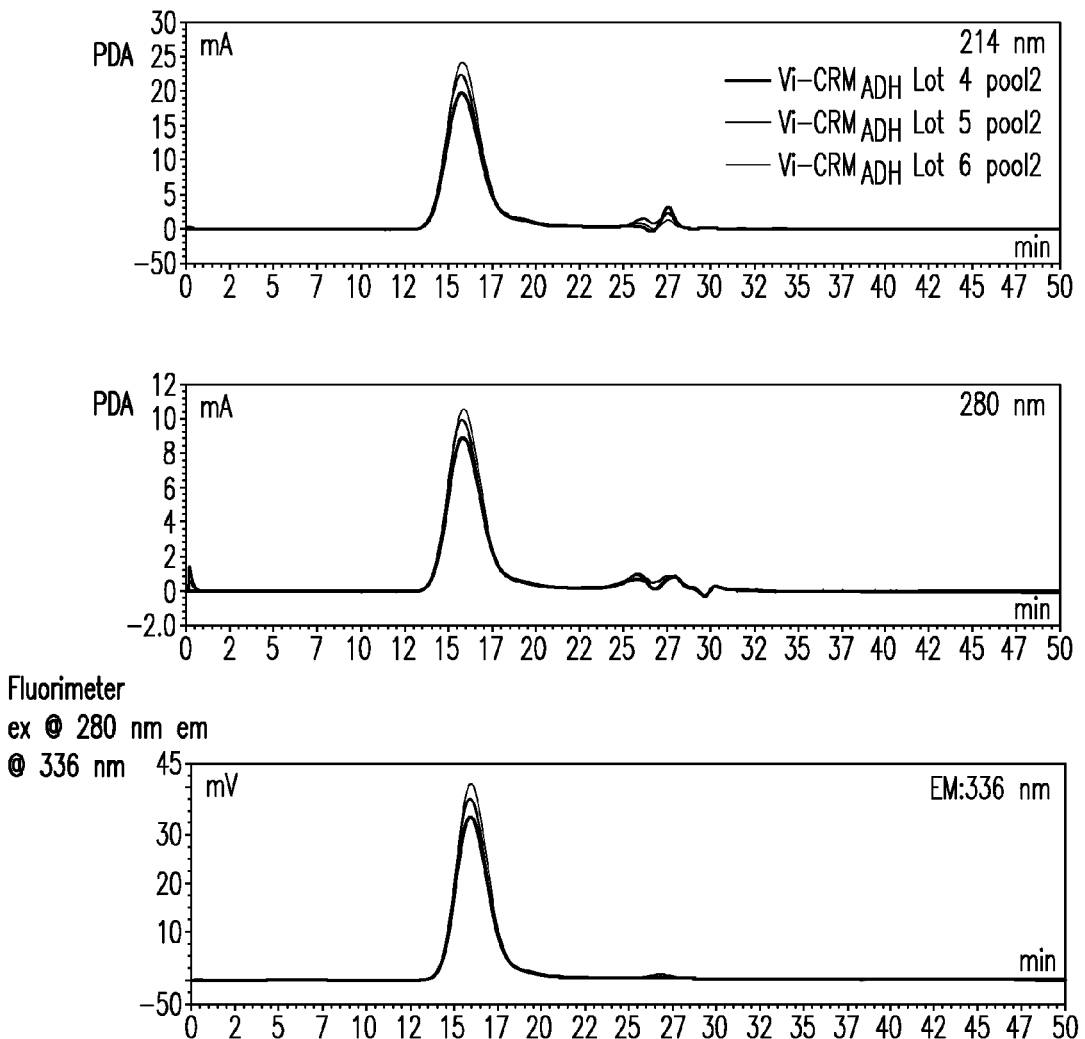
Figure 17:
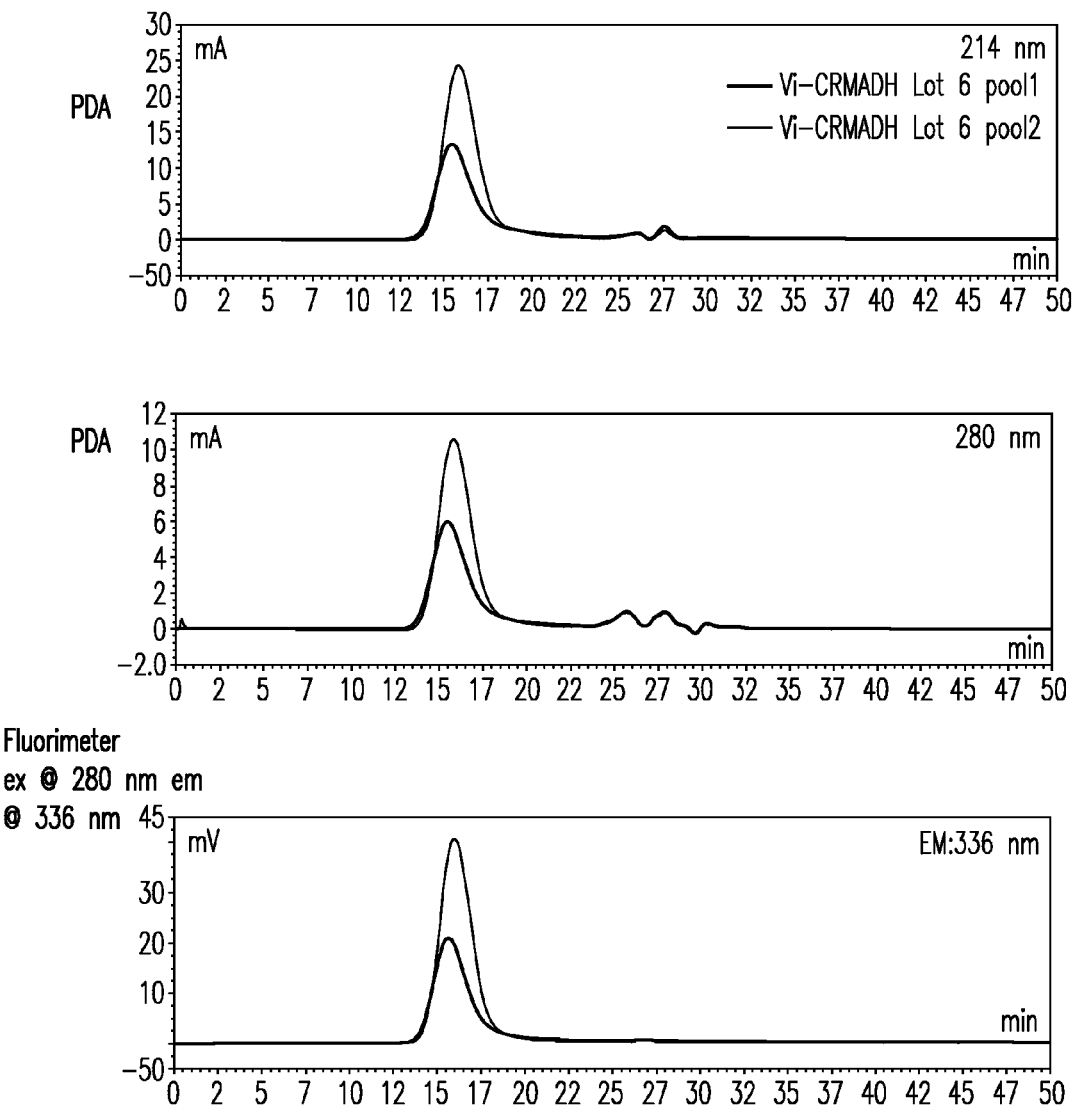

As an alternative means of purification, CRM$_{ADH}$ can be removed from the conjugate by tangential ultrafiltration FIGS. 15 to 17 show comparative SEC analyses of these pools (TSKgel 6000PW (TosoHaas) analytical column (7.5 mm×30.0 cm), eluent: 100 mM NaCl, 100 mM NaH$_2$PO$_4$, 5% CH$_3$CN, pH 7.2; Flow: 0.5 mL/min; V$_0$: ~13.5 min-V$_t$: ~27.8 min).

The conjugate was sterile filtered (0.22 µm), aliquoted and stored at −80° C. (4° C.).

Determination of In Vivo Activity

Antigens Used

The Vi–TT conjugates prepared in the previous example were used. Vi-CRM$_{ADH}$ Lot 03 was prepared using substantially the same conditions as Vi-CRM$_{ADH}$ Lots 04 to 06. Vi-CRM$_{ADH}$ Lot 01 was also prepared using substantially the same conditions as Vi-CRM$_{ADH}$ Lots 04 to 06, but with the difference that the ratio CRM$_{ADH}$/Vi (w) was equal to 1. The hyperimmune mouse serum immunized with Vi-rEPA was obtained from the NIH.

| Conjugate characteristics | | | |
|---|---|---|---|
| Conjugate | Protein content (micro BCA) | Saccharide content (acridine orange) | Ratio (w/w) saccharide/protein |
| a) Vi-CRM$_{ADH}$ Lot 01 | 3.18 mg | 3.65 mg | 1.15 |
| b) Vi-CRM$_{ADH}$ Lot 03 Pool 2 | 4.13 mg | 2.93 mg | 0.71 |
| c) Vi-TT$_{ADH}$ Pool 1 | 2.46 mg | 1.02 mg | 0.41 |
| d) Vi-TT$_{ADH}$ Pool 2 | 5.56 mg | 3.73 mg | 0.67 |

Study design

| Group | Immunization | Dose (μg) | N. injections | Bleed days | Route |
|---|---|---|---|---|---|
| 1 | PBS | — | 3 | 0, 14, 28, 42 | SC |
| 2 | Vi | 2.5 | 3 | 0, 14, 28, 42 | SC |
| 3 | Vi + CRM$_{ADH}$ | 2.5 | 3 | 0, 14, 28, 42 | SC |
| 4 | Vi + TT$_{ADH}$ | 2.5 | 3 | 0, 14, 28, 42 | SC |
| 5 | Vi-CRM$_{ADH}$ Lot 01 | 2.5 | 3 | 0, 14, 28, 42 | SC |
| 6 | Vi-CRM$_{ADH}$ Lot 03 Pool 2 | 2.5 | 3 | 0, 14, 28, 42 | SC |
| 7 | Vi-TT$_{ADH}$ Pool 1 | 2.5 | 3 | 0, 14, 28, 42 | SC |
| 8 | Vi-TT$_{ADH}$ Pool 2 | 2.5 | 3 | 0, 14, 28, 42 | SC |
| 9[a] | Vi-CRM$_{ADH}$ Lot 01 | 2.5 | 3 | 0, 14, 28, 42 | SC |
| 10[a] | Vi-CRM$_{ADH}$ Lot 03 Pool 2 | 2.5 | 3 | 0, 14, 28, 42 | SC |
| 11[a] | Vi-TT$_{ADH}$ Pool 1 | 2.5 | 3 | 0, 14, 28, 42 | SC |
| 12[a] | Vi-TT$_{ADH}$ Pool 2 | 2.5 | 3 | 0, 14, 28, 42 | SC |
| 13[b] | Vi-CRM$_{ADH}$ Lot 03 Pool 2 | 10 | 1-2-3 | 0, 14, 28, 42 | SC |
| 14[b] | Vi-CRM$_{ADH}$ Lot 03 Pool 2 | 10 | 1-2-3 | 0, 14, 28, 42 | SC |

[a] conjugates were adjuvanted with alum
[b] 1st immunization was adjuvanted with CFA, 2nd and 3rd immunizations with IFA Immunizations Balb/c female mice were divided in fourteen groups of eight mice each and were subcutaneously immunized with 2.5 μg of Vi, Vi-conjugate, or a physical mixture of Vi and ADH-derivatized carrier protein. Only groups 13 and 14 received 10 μg of immunization dose.

Three injections of 200 μl each were given every two weeks, with bleedings two weeks after each immunization.

Groups 9 to 12 received alum as adjuvant, while the adjuvant for groups 13 & 14 was complete Freund's adjuvant (CFA, 1st injection) and incomplete Freund's adjuvant (IFA, 2nd & 3rd injection).

ELISA Method

The wells of 96-well ELISA plates (Maxisorp, Nunc) were coated with 100 μl of 1 μg/ml Vi in carbonate buffer (0.05M, pH: 9.6) and left overnight at 4° C. Vi used for coating was purified from Citrobacter freundii WR7011. The following morning, the plates were blocked with 200 μl/well of 5% fat-free milk in PBS-TWEEN 20 (PBST, 0.05%) for 1 hour at room temperature (RT). After washing with PBST, 100 μl/well of mouse sera (1:200 diluted in PBST with 0.1% BSA) were incubated for 2 hours at RT. After three more washes, alkaline phosphatase-conjugated goat anti-mouse IgG secondary antibody (Sigma A3438, 1:10000 diluted in PBST, 0.1% BSA) was incubated at 100 μl/well for 1 hour at RT. Alkaline phosphatase substrate (p-NPP, Sigma N2765) was solved in diethanolamine buffer (1M, pH: 9.8) and was incubated after another wash for 1 hour at RT. Plates were read at 405 and 490 nm using an ELISA reader. Absorbance values used for antibody units determination were obtained by subtracting 490 nm to 405 nm values. Antibody units are expressed relative to a hyperimmune mouse anti-Vi standard serum, after Hill Plot analysis.

A hyperimmune mouse serum immunized with Vi-rEPA was used as internal positive control.

Each mouse serum was run in triplicate on three different ELISA plates and data are presented as arithmetic means and standard errors. One antibody unit is defined as the reciprocal of the dilution of the standard sera that gives an optical density equal to 1 in a standard ELISA.

Anti-CRM antibody values in groups 1, 2, 3, 5, 6, 9, 10, 13, 14

| Group | Immunization | Average | | | Standard Error | | |
|---|---|---|---|---|---|---|---|
| | | T14 | T28 | T42 | T14 | T28 | T42 |
| 1 | PBS | −0.41 | −0.64 | −0.77 | 0.12 | 0.14 | 0.09 |
| 2 | Vi | −0.89 | −0.58 | −0.65 | 0.14 | 0.17 | 0.07 |
| 3 | Vi + CRM | 0.09 | 34.88 | 256.81 | 0.25 | 16.11 | 42.99 |
| 5 | Vi-CRM$_{ADH}$ Lot 01 | 3.80 | 149.80 | 311.68 | 1.19 | 47.20 | 49.33 |
| 6 | Vi-CRM$_{ADH}$ Lot 03 Pool 2 | 7.30 | 163.06 | 550.38 | 2.64 | 50.91 | 44.70 |
| 9 | Vi-CRM$_{ADH}$ Lot 01/alum | 14.86 | 379.57 | 721.00 | 5.98 | 49.88 | 34.96 |
| 10 | Vi-CRM$_{ADH}$ Lot 03 Pool 2/alum | 44.73 | 263.46 | 452.91 | 7.27 | 16.74 | 29.09 |
| 13 | Vi-CRM$_{ADH}$ Lot 01 | 50.91 | 586.61 | 762.92 | 15.29 | 41.35 | 65.50 |
| 14 | Vi-CRM$_{ADH}$ Lot 01 | 69.18 | 672.56 | 841.66 | 22.68 | 53.35 | 43.42 |

Anti-Vi antibody values in all groups

| Group N. | Immunization | Average | | | Standard Error | | |
|---|---|---|---|---|---|---|---|
| | | T14 | T28 | T42 | T14 | T28 | T42 |
| 1 | PBS | 3.3 | −1.03 | −1.54 | 0.5 | 0.81 | 0.52 |
| 2 | Vi | −3.4 | −1.94 | −0.04 | 0.4 | 0.52 | 0.52 |
| 3 | Vi + CRM | 5.0 | −0.14 | 0.03 | 0.8 | 1.04 | 0.65 |
| 4 | Vi + TT | 1.1 | 2.51 | 1.31 | 1.3 | 1.23 | 0.39 |
| 5 | Vi-CRM$_{ADH}$ Lot 01 | 53.7 | 242.20 | 191.53 | 8.4 | 31.40 | 40.50 |
| 6 | Vi-CRM$_{ADH}$ Lot 03 Pool 2 | 95.4 | 245.39 | 225.66 | 40.9 | 45.33 | 38.00 |
| 7 | Vi-TT$_{ADH}$ Pool 1 | 75.5 | 170.20 | 160.49 | 18.0 | 27.17 | 34.25 |
| 8 | Vi-TT$_{ADH}$ Pool 2 | 58.2 | 126.23 | 126.20 | 13.1 | 18.50 | 17.74 |
| 9 | Vi-CRM$_{ADH}$ Lot 01/alum | 56.4 | 162.52 | 98.58 | 13.4 | 24.15 | 22.59 |
| 10 | Vi-CRM$_{ADH}$ Lot 03 Pool 2/alum | 58.7 | 98.92 | 93.22 | 18.8 | 24.87 | 30.55 |
| 11 | Vi-TT$_{ADH}$ Pool 1/alum | 44.6 | 191.81 | 151.56 | 18.3 | 36.76 | 38.83 |
| 12 | Vi-TT$_{ADH}$ Pool 2/alum | 68.1 | 202.99 | 180.09 | 18.0 | 24.89 | 21.73 |
| 13 | Vi-CRM$_{ADH}$ Lot 01 | 65.3 | 271.48 | 264.39 | 16.3 | 33.38 | 63.96 |
| 14 | Vi-CRM$_{ADH}$ Lot 01 | 134.5 | 202.51 | 234.78 | 32.2 | 86.61 | 64.27 |
| | NIH | | | 149.02 | | | 24.56 |

Figure 18A:
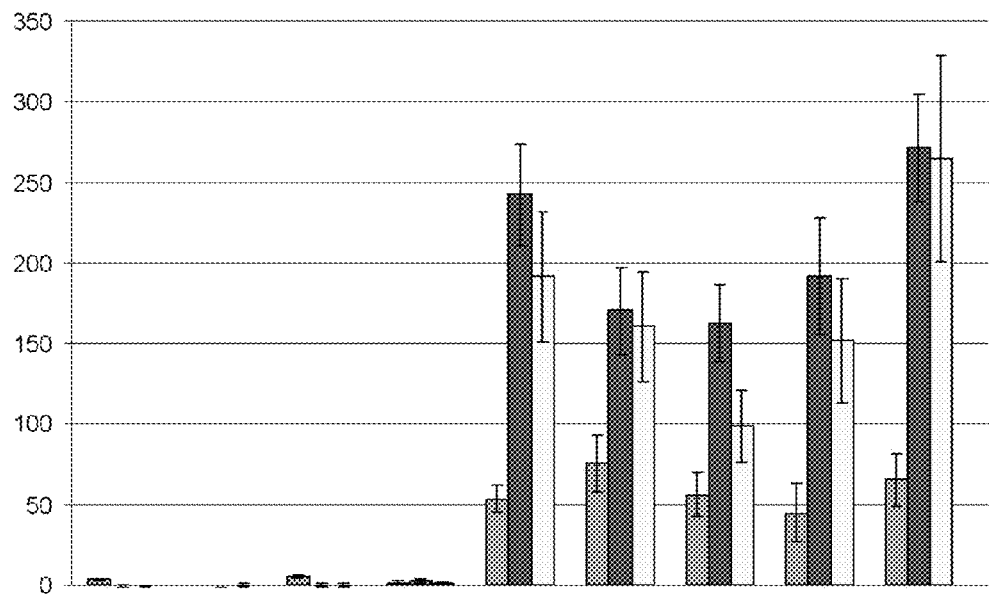
FIGS. 18A and 18B show data from different lots of conjugates, but the control groups are the same in each. From left to right the groups in both 18A and 18B are: PBS; Vi; Vi+CRM197; Vi+TT; Vi–CRM197; Vi–TT; Vi–CRM197 with alum; Vi–TT with alum; and Vi–CRM197 with CFA+IFA.
Figure 18B:
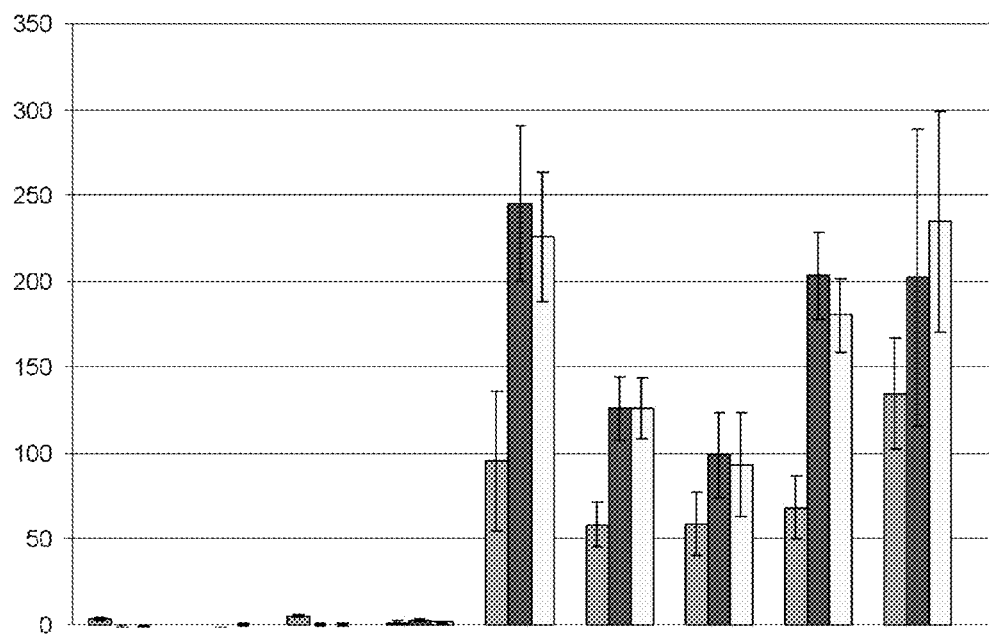

The results are plotted in FIG. 18.

Various modifications and variations of the present disclosure will be apparent to those skilled in the art without departing from the scope and spirit of the disclosure. Although the disclosure has been described in connection with specific preferred embodiments, it should be understood that the claims should not be unduly limited to such specific embodiments. Indeed, various modifications of the described modes for carrying out the disclosure, which are understood by those skilled in the art are intended to be within the scope of the claims.

REFERENCES

[1] Guzman et al. (2006) *Vaccine* 24(18):3804-11.
[2] Canh et al. (2004) *Infect Immun.* 72(11):6586-8.
[3] Kossaczka et al. (1997) *Infect Immun* 65(6):2088-93.
[4] Clark et al. (1958) *J Biol Chem* 230:81-89.
[5] Heyns et al. (1967) *Carbohydr Res* 3:340-353.
[6] Heyns et al. (1959) *Chem Ber* 92:2435-2438.
[7] Webster et al. (1954) *Arch Biochem Biophys* 50:223-224.
[8] Webster et al. (1954) *J Immunol* 73:16-22.
[9] Whiteside et al. (1961) *J Immunol* 86:538-542.
[10] Kao et al. (2004) *Vaccine* 22:335-344.
[11] Szu et al. (1991) *Infect Immun* 59(12):4555-61.
[12] Ravenscroft et al. (1999) *Vaccine* 17:2802-2816.
[13] Szu et al. (1994) *Infect Immun* 62(12):5545-9.
[14] WO 96/011709.
[15] US-A-2005/0106181.
[16] Inzana (1987) *Infect. Immun.* 55:1573-1579.
[17] WO98/32873.
[18] European patent 0072513.
[19] Lindberg (1999) *Vaccine* 17 Suppl 2:S28-36
[20] Buttery & Moxon (2000) *J R Coll Physicians Lond* 34:163-8
[21] Ahmad & Chapnick (1999) *Infect Dis Clin North Am* 13:113-33, vii
[22] Goldblatt (1998) *J. Med. Microbiol.* 47:563-567
[23] EP-B-0 477 508
[24] U.S. Pat. No. 5,306,492
[25] WO98/42721
[26] Dick et al. in *Conjugate Vaccines* (eds. Cruse et al.) Karger, Basel, 1989, Vol. 10, 48-114
[27] Hermanson *Bioconjugate Techniques*, Academic Press, San Diego Calif. (1996)
[28] Ramsay et al. (2001) *Lancet* 357(9251):195-6
[29] WO99/42130
[30] WO98/42721
[31] U.S. Pat. No. 4,882,317
[32] U.S. Pat. No. 4,695,624
[33] *Mol. Immunol.*, 1985, 22, 907-919
[34] EP-A-0208375
[35] Bethell G. S. et al., *J. Biol. Chem.*, 1979, 254, 2572-4
[36] Hearn M. T. W., *J. Chromatogr.*, 1981, 218, 509-18
[37] U.S. Pat. No. 4,965,338
[38] WO00/10599.
[39] Gever et al., Med. Microbial. Immunol, 165: 171-288 (1979).
[40] U.S. Pat. No. 4,057,685.
[41] U.S. Pat. Nos. 4,673,574; 4,761,283; 4,808,700.
[42] U.S. Pat. No. 4,459,286.
[43] U.S. Pat. No. 5,204,098
[44] U.S. Pat. No. 4,663,160.
[45] WO2007/000343.
[46] Szu et al. (1987) *J Exp Med* 1166(5):1510-24.
[47] *Research Disclosure*, 453077 (January 2002)
[48] EP-A-0372501.
[49] EP-A-0378881.
[50] EP-A-0427347.
[51] WO93/17712
[52] WO94/03208.
[53] WO98/58668.
[54] EP-A-0471177.
[55] WO91/01146
[56] Falugi et al. (2001) *Eur J Immunol* 31:3816-3824.
[57] Baraldo et al. (2004) *Infect Immun* 72(8):4884-7.
[58] EP-A-0594610.
[59] Ruan et al. (1990) *J Immunol* 145:3379-3384.
[60] WO00/56360.
[61] Kuo et al. (1995) *Infect Immun* 63:2706-13.
[62] Michon et al. (1998) *Vaccine.* 16:1732-41.
[63] WO02/091998.
[64] WO01/72337
[65] WO00/61761.
[66] WO00/33882
[67] WO99/42130
[68] WO96/40242
[69] Gennaro (2000) *Remington: The Science and Practice of Pharmacy.* 20th edition, ISBN: 0683306472.
[70] Almeida & Alpar (1996) *J. Drug Targeting* 3:455-467.
[71] U.S. Pat. No. 6,355,271.
[72] WO00/23105.
[73] U.S. Pat. No. 5,057,540.
[74] WO96/33739.
[75] EP-A-0109942.
[76] WO96/11711.
[77] WO00/07621.
[78] Barr et al. (1998) *Advanced Drug Delivery Reviews* 32:247-271.
[79] Sjolanderet et al. (1998) *Advanced Drug Delivery Reviews* 32:321-338.
[80] Pizza et al. (2000) *Int J Med Microbiol* 290:455-461.
[81] WO95/17211.
[82] WO98/42375.
[83] Singh et al] (2001) *J Cont Release* 70:267-276.
[84] WO99/27960.
[85] U.S. Pat. No. 6,090,406
[86] U.S. Pat. No. 5,916,588
[87] EP-A-0626169.
[88] Dyakonova et al. (2004) Int Immunopharmacol 4(13): 1615-23.
[89] FR-2859633.
[90] De Libero et al, *Nature Reviews Immunology*, 2005, 5: 485-496
[91] U.S. Pat. No. 5,936,076.
[92] Oki et al, *J. Clin. Investig.*, 113: 1631-1640
[93] US2005/0192248
[94] Yang et al, *Angew. Chem. Int. Ed.*, 2004, 43: 3818-3822
[95] WO2005/102049
[96] Goff et al, *J. Am. Chem., Soc.*, 2004, 126: 13602-13603
[97] WO03/105769
[98] Cooper (1995) *Pharm Biotechnol* 6:559-80.
[99] Kandimalla et al. (2003) *Nucleic Acids Research* 31:2393-2400.
[100] WO02/26757.
[101] WO99/62923.
[102] Krieg (2003) *Nature Medicine* 9:831-835.
[103] McCluskie et al. (2002) *FEMS Immunology and Medical Microbiology* 32:179-185.

[104] WO98/40100.
[105] U.S. Pat. No. 6,207,646.
[106] U.S. Pat. No. 6,239,116.
[107] U.S. Pat. No. 6,429,199.
[108] Kandimalla et al. (2003) *Biochemical Society Transactions* 31 (part 3):654-658.
[109] Blackwell et al. (2003) *J Immunol* 170:4061-4068.
[110] Krieg (2002) *Trends Immunol* 23:64-65.
[111] WO01/95935.
[112] Kandimalla et al. (2003) *BBRC* 306:948-953.
[113] Bhagat et al. (2003) *BBRC* 300:853-861.
[114] WO03/035836.
[115] WO01/22972.
[116] Schellack et al. (2006) *Vaccine* 24:5461-72.
[117] Myers et al. (1990) pages 145-156 of *Cellular and molecular aspects of endotoxin reactions*.
[118] Ulrich (2000) Chapter 16 (pages 273-282) of reference 156.
[119] Johnson et al. (1999) *J Med Chem* 42:4640-9.
[120] Baldrick et al. (2002) *Regulatory Toxicol Pharmacol* 35:398-413.
[121] WO 94/21292.
[122] Signorelli & Hadden (2003) *Int Immunopharmacol* 3(8):1177-86.
[123] WO2004/064715.
[124] U.S. Pat. No. 4,680,338.
[125] U.S. Pat. No. 4,988,815.
[126] WO92/15582.
[127] Stanley (2002) *Clin Exp Dermatol* 27:571-577.
[128] Wu et al. (2004) *Antiviral Res.* 64(2):79-83.
[129] Vasilakos et al. (2000) *Cell Immunol.* 204(1):64-74.
[130] U.S. Pat. Nos. 4,689,338, 4,929,624, 5,238,944, 5,266,575, 5,268,376, 5,346,905, 5,352,784, 5,389,640, 5,395,937, 5,482,936, 5,494,916, 5,525,612, 6,083,505, 6,440,992, 6,627,640, 6,656,938, 6,660,735, 6,660,747, 6,664,260, 6,664,264, 6,664,265, 6,667,312, 6,670,372, 6,677,347, 6,677,348, 6,677,349, 6,683,088, 6,703,402, 6,743,920, 6,800,624, 6,809,203, 6,888,000 and 6,924,293.
[131] Jones (2003) *Curr Opin Investig Drugs* 4:214-218.
[132] WO2004/060308.
[133] WO2004/064759.
[134] U.S. Pat. No. 6,924,271.
[135] US2005/0070556.
[136] U.S. Pat. No. 5,658,731.
[137] U.S. Pat. No. 5,011,828.
[138] WO2004/87153.
[139] U.S. Pat. No. 6,605,617.
[140] WO02/18383.
[141] WO2004/018455.
[142] WO03/082272.
[143] Johnson et al. (1999) *Bioorg Med Chem Lett* 9:2273-2278.
[144] Evans et al. (2003) *Expert Rev Vaccines* 2:219-229.
[145] Andrianov et al. (1998) *Biomaterials* 19:109-115.
[146] Payne et al. (1998) *Adv Drug Delivery Review* 31:185-196.
[147] WO03/011223.
[148] Meraldi et al. (2003) *Vaccine* 21:2485-2491.
[149] Pajak et al. (2003) *Vaccine* 21:836-842.
[150] Wong et al. (2003) *J Clin Pharmacol* 43(7):735-42.
[151] US2005/0215517.
[152] WO90/14837.
[153] Podda & Del Giudice (2003) *Expert Rev Vaccines* 2:197-203.
[154] Podda (2001) *Vaccine* 19: 2673-2680.
[155] *Vaccine Design: The Subunit and Adjuvant Approach* (eds. Powell & Newman) Plenum Press 1995 (ISBN 0-306-44867-X).
[156] *Vaccine Adjuvants: Preparation Methods and Research Protocols* (Volume 42 of *Methods in Molecular Medicine* series). ISBN: 1-59259-083-7. Ed. O'Hagan.
[157] Allison & Byars (1992) *Res Immunol* 143:519-25.
[158] Hariharan et al. (1995) *Cancer Res* 55:3486-9.
[159] WO95/11700.
[160] U.S. Pat. No. 6,080,725.
[161] WO2005/097181.

The invention claimed is:

1. A method of producing a conjugate of Vi capsular polysaccharide of *Salmonella typhi* comprising the steps of:
   (a) Simultaneously adding adipic acid dihydrazide (ADH) linker and 1-ethyl-3(3-dimethylaminopropyl) carbodiimide (EDAC) to a solution containing a carrier protein;
   (b) Removing excess of the ADH linker from the solution to provide an ADH-derivatized carrier protein;
   (c) Reacting the Vi capsular polysaccharide with EDAC, wherein the molar ratio of the COOH groups of the Vi capsular polysaccharide to the EDAC is >5:1, to provide an activated Vi capsular polysaccharide; and (d) Reacting the ADH-derivatized carrier protein of step (b) with the activated Vi capsular polysaccharide of step (c) to produce the conjugate of the Vi capsular polysaccharide.

2. The method of claim 1, wherein the molar ratio is >9:1.

3. The method of claim 1, wherein the carrier protein is CRM197.

4. The method of claim 2, wherein the carrier protein is CRM197.

5. The method of claim 1, wherein the excess of the ADH linker is removed by dialysis.

* * * * *

SEQUENCE LISTING

<160> NUMBER OF SEQ ID NOS: 1

<210> SEQ ID NO 1
<211> LENGTH: 11
<212> TYPE: PRT
<213> ORGANISM: Artificial sequence
<220> FEATURE:
<223> OTHER INFORMATION: synthetic peptide

<400> SEQUENCE: 1

Lys Leu Lys Leu Leu Leu Leu Leu Lys Leu Lys
1               5                   10